US008822484B2

(12) United States Patent
Srivastava et al.

(10) Patent No.: US 8,822,484 B2
(45) Date of Patent: Sep. 2, 2014

(54) FUSED THIAZOLO AND OXAZOLO PYRIMIDINONES

(71) Applicant: Torrent Pharmaceuticals Limited, Gujarat (IN)

(72) Inventors: Sanjay Srivastava, Gujrat (IN); Laxmikant Chhipa, Gujrat (IN); Ramesh Chandra Gupta, Gujrat (IN); Shailesh Deshpande, Gujrat (IN); Anita Chaudhari, Gujrat (IN); Anookh Mohanan, Gujrat (IN); Chaitanya Dutt, Gujrat (IN); Vijay Chauthaiwale, Gujrat (IN); Murali Badanthadka, Gujrat (IN); Prashant G. Jamadarkhana, Gujrat (IN)

(73) Assignee: Torrent Pharmaceuticals Limited, Ahmedabad, Gujarat (IN)

( * ) Notice: Subject to any disclaimer, the term of this patent is extended or adjusted under 35 U.S.C. 154(b) by 0 days.

(21) Appl. No.: 13/963,160

(22) Filed: Aug. 9, 2013

(65) Prior Publication Data
US 2013/0331406 A1    Dec. 12, 2013

Related U.S. Application Data

(62) Division of application No. 12/877,704, filed on Sep. 8, 2010, now Pat. No. 8,541,430.

(60) Provisional application No. 61/264,734, filed on Nov. 27, 2009.

(51) Int. Cl.
*A61K 31/519* (2006.01)
*A61K 31/55* (2006.01)
*C07D 513/04* (2006.01)
*C07D 513/14* (2006.01)

(52) U.S. Cl.
CPC ............ *C07D 513/04* (2013.01); *C07D 513/14* (2013.01)
USPC ........................................................ 514/267

(58) Field of Classification Search
USPC .......................................... 514/267; 544/250
See application file for complete search history.

(56) References Cited

U.S. PATENT DOCUMENTS

| 4,423,048 | A | 12/1983 | Kadin |
| 2006/0252837 | A1 | 11/2006 | Ohta et al. |

FOREIGN PATENT DOCUMENTS

| EP | 0 661 269 A1 | 7/1995 |
| JP | 05-039293 | 2/1993 |
| WO | WO 03/049686 A2 | 6/2003 |
| WO | WO 03/053997 A2 | 7/2003 |
| WO | WO 2004/108121 A1 | 12/2004 |
| WO | WO 2007/146425 A2 | 12/2007 |
| WO | WO 2007/146438 A1 | 12/2007 |
| WO | WO 2009/039321 | * 3/2009 ........... A61K 31/415 |
| WO | WO 2009/039321 A1 | 3/2009 |
| WO | WO 2009/039322 A1 | 3/2009 |

OTHER PUBLICATIONS

Bernhardt, et al., Inhibition of Prolyl Hydroxylases Increases Erythropoietin Production in ESRD. J. Am. Soc. Nephrol. 21, 2151-2156 (2010).*
Zhu et al., "Novel p53 inactivators with neuroprotective action: Syntheses and pharmacological evaluation of 2-Imino-2,3,4,5,6,7-hexahydrobenzothiazole and 2-Imino-2,3,4,5,6,7-hexahydrobenzoxazole derivatives," *J. Med. Chem.* (2002) 45: 5090-5097.
Berge et al., "Pharmaceutical salts," *Journal of Pharmaceutical Sciences* (1977) 66 (1): 1-19.
Shapiro et al., "Attenuation of hypermetabolism in the remnant kidney by dietary phosphate restriction in the rat," *Am. J. Physiol.* (1990) 258: 183-188.
Priyadarshi et al., "Effects of reduction of renal mass on renal oxygen tension and erythropoietin production in the rat," *Kidney International* (2002) 61: 542-546.
Hahn et al., "Vitamin E suppresses oxidative stress and glomerulosclerosis in rat remnant kidney," *Pediatr. Nephrol.* (1999) 13: 195-198.
Looi et al., "Adrenonedullin acts via nitric oxide and peroxynitrite to protect against myocardial ischaemia-induced arrhythmias in anaesthetized rats," *British Journal of Pharmacology* (2006) 148: 599-609.
Sharples et al., "Erythropoietin protects the kidney against the injury and dysfunction caused by ischemia-reperfusion," *J. Am. Soc. Nephrol.* (2004) 15: 2115-2124.
Siren et al., "Erythropoietin prevents neuronal apoptosis after cerebral ischemia and metabolic stress," *PNAS* (2001) 98 (7): 4044-4049.
Luo et al., "Pretreatment with erythropoietin reduces hepatic ischemia-reperfusion injury," *Hepatobiliary Pancreat. Dis. Int.* (2009) 8 (3): 294-299.
Binley et al., "Long-term reversal of chronic anemia using a hypoxia-regulated erythropoietin gene therapy," *Blood* (2002) 100: 2406-2413.
Fisher, J.W., "Erythropoietin: Physiology and pharmacology update," *Exp. Biol. Med.* (2003) 228: 1-14.

(Continued)

*Primary Examiner* — Erich A Leeser
(74) *Attorney, Agent, or Firm* — Merchant & Gould P.C.

(57) ABSTRACT

The present invention relates to novel compounds, their pharmaceutically acceptable salts, and their isomers, steroisomers, conformers, tautomers, polymorphs, hydrates and solvates. The present invention also encompasses pharmaceutically acceptable compositions of said compounds and process for preparing novel compounds. The invention further relates to the use of the above-mentioned compounds for the preparation of medicament for use as pharmaceuticals.

6 Claims, No Drawings

(56) References Cited

OTHER PUBLICATIONS

Amador et al., "Ischemic pre-conditioning in deceased donor liver transplantation: A prospective randomized clinical trial," *American Journal of Transplantation* (2007) 7: 2180-2189.

Nangaku, M., "The heat is on: An expanding role for hypoxia-inducible factors in kidney transplantation," *J. Am. Soc. Nephrol.* (2007) 18: 13-15.

Siddiq et al., "Hypoxia-inducible factor prolyl 4-hydroxylase inhibition," *The Journal of Biological Chemistry* (2005) 280 (50): 41732-41743.

Hill et al., "Inhibition of hypoxia inducible factor hydroxylases protects against renal ischemia-reperfusion injury," *J. Am. Soc. Nephrol.* (2008) 19: 39-46.

Bernhardt et al., "Preconditional activation of hypoxia-inducible factors ameliorates ischemic acute renal failure," *J. Am. Soc. Nephrol.* (2006) 17: 1970-1978.

Weidemann et al., "HIF activation protects from acute kidney injury," *J. Am. Soc. Nephrol.* (2008) 19: 486-494.

Semenza, G.L., "HIF-1: mediator of physiological and pathophysiological responses to hypoxia," *J. Appl. Physiol.* (2000) 88: 1474-1480.

Schofield et al., "Oxygen sensing by HIF hydroxylases," *Nature Reviews* (2004) 5: 343-354.

Non-Final Office Action from U.S. Appl. No. 12/877,704 mailed Oct. 26, 2012.

West, Anothony R., Solid State Chemistry and Its Applications, Wiley, New York, 1988, 358.

Kato et al., "Adrenomedullin gene delivery attenuates myocardial infarction and apoptosis after ischemia and reperfusion", *Am J Physiol Heart Circ Physiol*, vol. 285, 2003, pp. H1506-H1514.

Kato et al., "Effect of Erythropoietin on Angiogenesis With the Increased Adhesion of Platelets to the Microvessels in the Hind-Limb Ischemia Model in Mice", *J. Pharmacol Sci*, vol. 112, 2010, pp. 167-175.

Koransky et al., "VEGF Gene Delivery for Treatment of Ischemic Cardiovascular Disease", *Trends Cardiovasc Med*, vol. 12, No. 3, 2002, pp. 108-114.

Macdougall, Iain C., "Novel Erythropiesis-Stimulating Agents: A New Era in Anemia Management", *Clin J Am Soc Nephrol*, vol. 3, 2008, pp. 200-207.

Minnerup et al., "The Efficacy of Erythropoietin and Its Analogues in Animal Stroke Models: A Meta-Analysis", *Stroke*, vol. 40, 2009, pp. 3113-3120.

Rui et al., "Erythropoietin prevents the acute myocardial inflammatory response induced by ischemia/reperfusion via induction of AP-1", *Cardiovascular Research*, vol. 65, 2005, pp. 719-727.

Shah et al., "Attenuation of renal ischemia and reperfusion injury by human adrenomedullin and its binding protein",*J Surg Res*, vol. 163, No. 1, 2010, pp. 110-117.

van der Putten et al., "Mechanisms of Disease: erythropoietin resistance in patients with both heart and kidney failure", *Nature Clinical Practice Nephrology*, vol. 4, No. 1, 2008, pp. 47-56.

Yang et al., "Human Adrenomedullin and Its Binding Protein Attenuate Organ Injury and Reduce Mortality After Hepatic Ischemia-Reperfusion", *Ann Surg.*, vol. 249, No. 2, 2009, pp. 310-317.

Yazihan et al., "Protective Effect of Erythropoietin in Renal Ischemia-Reperfusion Injury", *The Open Drug Discovery Journal*, vol. 2, 2010, pp. 3-7.

\* cited by examiner

FUSED THIAZOLO AND OXAZOLO PYRIMIDINONES

CROSS REFERENCE TO RELATED APPLICATIONS

This application is a Divisional application of U.S. application Ser. No. 12/877,704 filed 8 Sep. 2010, which claims priority to U.S. Application Ser. No. 61/264,734 filed on Nov. 27, 2009, and which applications is incorporated herein by reference. To the extent appropriate, a claim of priority is made to each of the above disclosed applications.

FIELD OF THE INVENTION

The present invention relates to novel thiazolo and oxazolo pyrimidinone compounds of formula (I), their pharmaceutically acceptable salts, and their isomers, steroisomers, conformers, tautomers, polymorphs, hydrates and solvates. The present invention also encompasses pharmaceutically acceptable compositions of said compounds and process for preparing novel compounds. The invention further relates to the use of the above-mentioned compounds for the preparation of medicament for use as pharmaceuticals.

BACKGROUND OF THE INVENTION

The transcription factor HIF (Hypoxia Inducible Factor) has a central role in oxygen homeostasis. An early response to tissue hypoxia is induction of Hypoxia Inducible Factor (HIF), a basic helix-loop-helix (bHLH) PAS (Per/Arnt/Sim) transcriptional activator that mediates changes in gene expression in response to changes in cellular oxygen concentration. HIF is a heterodimer consisting of a constitutively expressed beta subunit and one of the two alpha subunits, HIFα1 and HIFα2.[1]

In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus and activates the expression of several genes including glycolytic enzymes, glucose transporter (GLUT)-1, erythropoietin (EPO), vascular endothelial growth factor (VEGF) and adrenomedullin.[1]

Thus, HIF activation is one of the prominent adaptive mechanisms associated with hypoxia/ischemia. As mentioned, HIF activation results in enhanced expression of genes which perform multiple functions to cope up with and to recover from hypoxic/ischemic conditions.[2]

In oxygenated cells (normoxic), two conserved proline residues of HIFα subunits undergo hydroxylation. This reaction is catalysed by HIF prolyl-hydroxylases (PHD). Prolyl hydroxylated HIFα interacts with pVHL and rapidly gets degraded by proteasome machinery. In addition, in normoxic cells, one conserved asparagine of HIFα also undergoes hydroxylation. This reaction is catalysed by HIF aspargyl hydroxylase (FIH). Aspargyl hydroxylated HIFα can not interact with transcriptional co-activator CBP/p300.

Under hypoxic/ischemic conditions, both HIF prolyl and HIF aspargyl hydroxylase activities are drastically lowered due to limiting amount of molecular oxygen. As a result, HIFα is not destined for proteasome degradation and hence stabilized. Further, HIFα can interact with transcriptional co-activator CBP/p300. Such stabilized and transcriptionally active HIFα then forms heterodimer with HIF-beta subunit and translocates to the nucleus and bring about transactivation of HIF target genes[1].

Inhibition of HIF prolyl hydroxylases and HIF asparagyl hydroxylase, thus can be a powerful approach for oxygen-independent activation of HIF. Such HIF activation by pharmacological means results in enhanced expression of genes which perform multiple functions to cope up with and to recover from hypoxic/ischemic conditions. HIF targets include genes responsible for vasomotor regulation (e.g. Adrenomedullin, eNOS, Haem Oxygrenase), energy metabolism (e.g. Glut-1, carbonic anhydrase-9), angiogenic signaling (e.g. VEGF, VEGF receptor-1) and erythropoiesis (e.g. Erythropoietin, Transferrin, transferrin receptor)[1]. Therefore, HIF activation can offer significant therapeutic benefits in various disease conditions such as anemia of various types and tissue injuries caused by hypoxia/ischemia in conditions like acute kidney injury, myocardial infarction, stroke, hepatic ischemia-reperfusion injury, peripheral vascular diseases and transplantation of liver or kidney[3,4,5,6,7,8]

Anemia is characterised by decrease in normal number of red blood cells, which is generally caused by loss of blood (hemorrhage), excessive red blood cell destruction (hemolysis) or deficient red blood cell production (ineffective hematopoiesis). Since hemoglobin normally carries oxygen from the lungs to the tissues, anemia leads to hypoxia in organs. Since all human cells depend on oxygen for survival, anemia can have a wide range of clinical consequences.

Anemia occurs often in elderly, in cancer patients, particularly those receiving chemotherapy & undergoing radiation, patients with renal diseases and in a wide variety of conditions associated with chronic diseases. Frequently, the cause of anemia is reduced erythropoietin (EPO) production resulting in prevention of erythropoiesis.

Erythropoietin (EPO), a naturally occurring hormone that is produced in response to HIFα, stimulates the production of erythrocytes. EPO is normally secreted by the kidneys, and endogenous EPO is increased under conditions of reduced oxygen (hypoxia)[9].

Exogeneous administration of EPO is one of the accepted modalities of treatment of anemia particularly in chronic renal failure patients, cancer patients undergoing radiation and/or chemotherapy; however its use is limited by high cost and increased risk for thrombosis and hypertension[10].

Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

Ischemia can be an acute (sudden onset and short duration) or chronic (slow onset with long duration or frequent recurrence). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain, and heart, producing disorders such as intestinal infarction, pulmonary infarction, ischemic stroke, and myocardial infarction.

Ischemic and hypoxic disorders are a major cause of morbidity and mortality.

Currently, treatment of ischemic and hypoxic disorders is focused on relief of symptoms and treatment of causative disorders but none of these therapies directly address the tissue damage produced by the ischemia and hypoxia.

Exogenous administration of some of the HIF target genes such as erythropoietin, VEGF, adrenomedullin has shown significant functional recovery in ischemia and ischemia-reperfusion injury of heart, kidney, brain and liver.[11,12,13,14]

Due to deficiencies in current treatments of anemia & diseases due to hypoxia and ischemia, there remains a need for compounds that are effective in treating anemias of different types such as anemia in elderly or anemia associated with chronic diseases or renal failure or cancer or infection or dialysis or surgery or chemotherapy and in ischemic/hypoxic disorders such as acute kidney injury, myocardial infarction, stroke, hepatic ischemia-reperfusion injury and peripheral vascular diseases.

The compounds of this invention provide a means for inhibiting HIF hydroxylases and thereby activating the HIF, which results in enhanced expression of the wide spectrum of target genes including erythropoietin (EPO), vascular endothelial growth factor (VEGF), adrenomedullin etc. and thus useful in treating various disorders including anemia of different types and conditions associated with ischemia/hypoxia.

EP 661269 discloses substituted heterocyclic carboxylic acid amides and their use as inhibitors of prolyl-4-hydroxylase and as inhibitors of collagen biosynthesis.

Additionally, various patent publications such as WO2003049686, WO2003053997, WO2004108121, WO2007146425, WO2007146438 disclose the compounds that stabilize HIFα and their use for the prevention and treatment of conditions associated with ischemia & hypoxia and EPO associated conditions like anemia and neurological disorders.

JP 5039293 discloses a various fused and substituted thiazolopyrimidine derivative or it's salt, useful as an immunomodulating agent.

International publications WO2009039321 and WO2009039322 disclose bicyclic heteroaromatic N-substituted glycine derivatives, which are antagonists of HIF prolyl hydroxylases and are useful for treating diseases benefiting from the inhibition of these enzymes like anemia.

SUMMARY OF THE INVENTION

In one embodiment, the present invention provides novel compounds of formula (I),

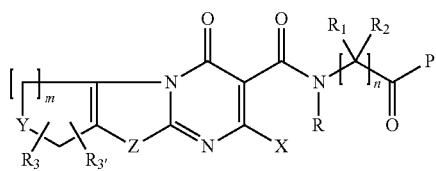

their pharmaceutically acceptable salts and their isomers, stereoisomers, conformers, tautomers, polymorphs, hydrates, and solvates;
Wherein,
when Y is $NR_4$, O, S or $SO_2$, m is 1 to 2 and when Y is $C(R_5)(R_6)$, m is 1 to 4;
n is 1 to 6;
P is —OH, —$OR_7$, —$NH_2$, —$NHR_7$, —$NR_7R_{7'}$, —$NHSO_2R_7$, —$NHCOR_7$, —NHOH or —$NHOR_7$;
X is —OH, —$OR_7$, —$SR_7$, —$SOR_7$, —$SO_2R_7$, —$NHR_7$ or —$NR_7R_{7'}$;
Z is S or O;

R is hydrogen, linear or branched $(C_1-C_8)$alkyl, —$(C_1-C_8)$alkylaryl or —$(C_1-C_8)$alkylheteroaryl;
$R_1$ and $R_2$ are independently selected from hydrogen, linear or branched —$(C_1-C_8)$alkyl, —$(C_3-C_7)$ cycloalkyl, aryl, heteroaryl, —$CH_2$-aryl and —$CH_2$-heteroaryl, or
$R_1$ and $R_2$ may join together to form a 3-6 membered monocyclic or 9-12 membered bicyclic ring;
R together with either $R_1$ or $R_2$ of adjacent carbon atom may form a 3-6 membered monocyclic or 8-11 membered bicyclic heteroaryl or heterocyclyl ring;
$R_3$ and $R_{3'}$ at each occurrence is independently selected from hydrogen, linear or branched $(C_1-C_8)$alkyl, $(C_1-C_5)$ alkoxy and halo;
$R_3$ and $R_{3'}$ may also present in gem di-halo, gem di-alkyl or spirocycloalkyl arrangement;
$R_4$ is selected from the group consisting of hydrogen, linear or branched $(C_1-C_8)$ alkyl, $(C_3-C_7)$ cycloalkyl, aryl, heteroaryl, —$(C_1-C_8)$ alkyl-aryl, —$(C_1-C_8)$alkyl-heteroaryl, —$(C_1-C_2)$ alkyl-heterocyclyl, —$C(O)R_8$, —$C(O)OR_8$, —$C(O)NR_8R_9$, —$C(S)NR_8R_9$ and —$SO_2R_8$, wherein aryl and heteroaryl radicals are optionally substituted with one or more substituent selected from the group consisting of —$(C_1-C_8)$ alkyl, —$(C_3-C_7)$ cycloalkyl, heterocyclyl, aryl, heteroaryl, —OH, -alkoxy, halo, CN, —$CF_3$, —$OCF_3$, —O-aryl, —$SO_2$—$(C_1-C_8)$-alkyl, —$SO_2$-aryl, —$NH_2$, —$NHR_{10}$, —$NR_{10}R_{10'}$, —NH—CO—$(C_1-C_8)$alkyl, —NH—$SO_2$—$(C_1-C_8)$alkyl, —NH—$SO_2$-aryl, —COOH, —C(O)NH-alkyl, —CONH-aryl, —CONH-heteroaryl, —C(O)O—$(C_1-C_8)$alkyl, —C(O)O-aryl, —$SO_2NH$—$(C_1-C_8)$alkyl, —$SO_2NH$-aryl and —$SO_2NH$-heteroaryl;
$R_5$ and $R_6$ are independently selected from the group consisting of hydrogen, linear or branched $(C_1-C_8)$alkyl, $(C_3-C_7)$ cycloalkyl, aryl, heteroaryl, fluoro, —COOH, —CONH—$(C_1-C_8)$alkyl, —NHCO—$(C_1-C_8)$alkyl, —NHCO-aryl, —NHCO-hetero aryl, —NH—$SO_2(C_1-C_8)$alkyl, —NH—$SO_2$-aryl and —NH—$SO_2$-heteroaryl;
$R_5$ and $R_6$ may join together to form a 3-6 membered carbocyclic, heteroaryl or heterocyclyl ring;
$R_7$, $R_{7'}$, $R_{10}$ and $R_{10'}$ are independently selected from linear or branched $(C_1-C_8)$alkyl, $(C_3-C_7)$ cycloalkyl and —$(C_1-C_8)$ alkylaryl;
$R_7$ and $R_{7'}$ or $R_{10}$ and $R_{10'}$ together with nitrogen atom to which they are attached, may form 5-6 membered monocyclic or 8-14 membered bicyclic saturated and partially saturated ring. The ring may contain 1 to 3 heteroatom selected from N, S & O. Wherein saturated and partially saturated ring may be optionally substituted with one or more substituent independently selected from the group consisting of —$(C_1-C_8)$alkyl, —$(C_3-C_7)$ cycloalkyl, heterocyclyl, aryl, heteroaryl, —OH, -alkoxy, halo, —CN, —$CF_3$, —$OCF_3$, —O-aryl, —$SO_2$—$(C_1-C_8)$-alkyl, —$SO_2$-aryl, —$NH_2$, —$NHR_{10}$, —$NR_{10}R_{10'}$, —NH—CO—$(C_1-C_8)$alkyl, —NH—$SO_2$—$(C_1-C_8)$alkyl, —NH—$SO_2$-aryl, —COOH, —C(O)NH-alkyl, —CONH-aryl, —CONH-heteroaryl, —C(O)O—$(C_1-C_8)$alkyl, —C(O)O-aryl, —$SO_2NH$—$(C_1-C_8)$alkyl, —$SO_2NH$-aryl and —$SO_2NH$-heteroaryl;
$R_8$ is selected from the group consisting of linear or branched $(C_1-C_8)$ alkyl, $(C_3-C_7)$ cycloalkyl, —$(C_1-C_8)$alkyl-$(C_3-C_7)$ cycloalkyl, heterocyclyl, aryl, —$(C_1-C_8)$alkyl-aryl, —$(C_1-C_2)$alkyl-heterocyclyl, heteroaryl and —$(C_1-C_8)$alkyl-heteroaryl, wherein aryl and heteroaryl radicals are optionally substituted with one or more substituent selected from linear or branched $(C_1-C_8)$alkyl, $(C_3-C_7)$cycloalkyl, —$(C_1-C_8)$ alkyl-$(C_3-C_7)$cycloalkyl, aryl, heteroaryl, heterocyclyl, —OH, alkoxy, halo, —CN, —$CF_3$, —$OCF_3$, —O-aryl, —$SO_2$—$(C_1-C_8)$alkyl, —$SO_2$-aryl, —$NH_2$, —$NHR_{10}$, —$NR_{10}R_{10'}$, —NH—CO—$(C_1-C_8)$alkyl, —NH—$SO_2$—

$(C_1-C_8)$alkyl, —C(O)OH, —C(O)NH—$(C_1-C_8)$alkyl, —CONH-aryl, —CONH-heteroaryl, —NHCONH—$(C_1-C_8)$alkyl, —NHCONH-aryl, —SO$_2$NH—$(C_1-C_8)$alkyl, —SO$_2$NH-aryl and —SO$_2$NH-heteroaryl;

$R_9$ is hydrogen, linear or branched $(C_1-C_8)$alkyl or —$(C_1-C_8)$alkylaryl;

$R_8$ and $R_9$ together with nitrogen atom to which they are attached, may form 5-6 membered saturated ring.

In another embodiment, the present invention pertains to a compound as above, however only including pharmaceutically acceptable salts thereof.

In another embodiment, the present invention includes synthetic intermediates that are useful in preparing the compounds of formula (I) and process for preparing such intermediates.

Another embodiment of the present invention is a method for preparation of a compound of formula (I) as herein described in Schemes A, B, C, D & E.

Another embodiment of the present invention is a pharmaceutical composition comprising a compound of formula (I), optionally in admixture with a pharmaceutically acceptable adjuvant, diluent or carrier.

Another embodiment of the present invention is a method for treating anemia by administering a therapeutically effective amount of a compound of formula (I) to a mammal in need thereof.

Another embodiment of the present invention is a method for treating anemia of elderly or anemia associated with conditions like chronic diseases, renal failure, cancer, infection, dialysis, surgery, and chemotherapy by administering a therapeutically effective amount of a compound of formula (I) to a mammal in need thereof.

Another embodiment of the present invention is a method for prevention or treatment of tissue damage caused by renal ischemia, cardiovascular ischemia, cerebrovascular ischemia, hepatic ischemia or peripheral vascular ischemia by administering a therapeutically effective amount of a compound of formula (I) to a mammal in need thereof.

Another embodiment of the present invention is a method for prevention or treatment of tissue damage caused by ischemic disorders including acute kidney injury, myocardial infarction, stroke, hepatic ischemia-reperfusion injury and peripheral vascular diseases by administering a therapeutically effective amount of a compound of formula (I) to a mammal in need thereof.

Another embodiment of the present invention is a method for prevention or treatment of tissue damage caused by ischemia-reperfusion injury while transplantation procedures of organs like liver or kidney by administering a therapeutically effective amount of a compound of formula (I) to a mammal in need thereof.

Another embodiment of the present invention is the use of a compound of formula (I) for the preparation of a medicament for treating anemia.

Another embodiment of the present invention is the use of a compound of formula (I) for the preparation of a medicament for treating anemia of elderly or anemia associated with conditions like chronic diseases, renal failure, cancer, infection, dialysis, surgery and chemotherapy.

Another embodiment of the present invention is the use of a compound of formula (I) for the preparation of a medicament for prevention or treatment of tissue damage caused by renal ischemia, cardiovascular ischemia, cerebrovascular ischemia, hepatic ischemia or peripheral vascular ischemia.

Another embodiment of the present invention is the use of a compound of formula (I) for the preparation of a medicament for prevention or treatment of tissue damage caused by ischemic disorders including acute kidney injury, myocardial infarction, stroke, hepatic ischemia-reperfusion injury and peripheral vascular diseases.

Another embodiment of the present invention is the use of a compound of formula (I) for the preparation of a medicament for prevention or treatment of tissue damage caused by ischemia-reperfusion injury while transplantation procedures of organs like liver or kidney.

DETAILED DESCRIPTION OF THE INVENTION

In one embodiment, the present invention provides novel compounds of formula (I),

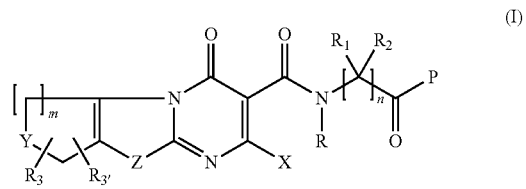

their pharmaceutically acceptable salts and their isomers, stereoisomers, conformers, tautomers, polymorphs, hydrates and solvates, wherein R, $R_1$, $R_2$, $R_3$, $R_{3'}$, X, Y, Z, m, n and P are as defined above.

A family of specific compounds of particular interest within the above formula (I) consists of compound and pharmaceutically acceptable salts thereof as follows:

| Compd. No. | Chemical Name |
|---|---|
| 1 | [(2-Hydroxy-4-oxo-5,6,7,8-tetrahydro-4H-9-thia-1,4a-diaza-fluorene-3-carbonyl)-amino]-acetic acid |
| 2 | 3-(Carboxymethyl-carbamoyl)-2-hydroxy-4-oxo-5,8-dihydro-4H,6H-9-thia-1,4a,7-triaza-fluorene-7-carboxylic acid ethyl ester |
| 3 | [(2-Hydroxy-7-methanesulfonyl-4-oxo-5,6,7,8-tetrahydro-4H-9-thia-1,4a,7-triaza-fluorene-3-carbonyl)-amino]-acetic acid |
| 4 | {[2-Hydroxy-7-(3-methyl-butyryl)-4-oxo-5,6,7,8-tetrahydro-4H-9-thia-1,4a,7-triaza-fluorene-3-carbonyl]-amino}-acetic acid |
| 5 | {[2-Hydroxy-4-oxo-7-(propane-2-sulfonyl)-5,6,7,8-tetrahydro-4H-9-thia-1,4a,7-triaza-fluorene-3-carbonyl]-amino}-acetic acid |
| 6 | 1-[(2-Hydroxy-4-oxo-5,6,7,8-tetrahydro-4H-9-thia-1,4a-diaza-fluorene-3-carbonyl)-amino]-cyclopentanecarboxylic acid |
| 7 | {[2-Hydroxy-4-oxo-7-(toluene-4-sulfonyl)-5,6,7,8-tetrahydro-4H-9-thia-1,4a,7-triaza-fluorene-3-carbonyl]-amino}-acetic acid |
| 8 | [(2-Hydroxy-4-oxo-7-phenylcarbamoyl-5,6,7,8-tetrahydro-4H-9-thia-1,4a,7-triaza-fluorene-3-carbonyl)-amino]-acetic acid |

-continued

| Compd. No. | Chemical Name |
|---|---|
| 9 | [(7-Cyclopropanecarbonyl-2-hydroxy-4-oxo-5,6,7,8-tetrahydro-4H-9-thia-1,4a,7-triaza-fluorene-3-carbonyl)-amino]-acetic acid |
| 10 | [(2-Hydroxy-4-oxo-6,7,8,9-tetrahydro-4H,5H-10-thia-1,4a-diaza-benzo[a]azulene-3-carbonyl)-amino]-acetic acid |
| 11 | [(2-Hydroxy-4-oxo-7,8-dihydro-4H,6H-cyclopenta[4,5]thiazolo[3,2-a]pyrimidine-3-carbonyl)-amino]-acetic acid |
| 12 | [(2-Hydroxy-4-oxo-5,6,7,8-tetrahydro-4H-9-thia-1,4a-diaza-fluorene-3-carbonyl)-amino]-acetic acid, sodium salt |
| 13 | [(7-tert-Butyl-2-hydroxy-4-oxo-5,6,7,8-tetrahydro-4H-9-thia-1,4a-diaza-fluorene-3-carbonyl)-amino]-acetic acid |
| 14 | 3-[(2-Hydroxy-4-oxo-7,8-dihydro-4H,6H-cyclopenta[4,5]thiazolo[3,2-a]pyrimidine-3-carbonyl)-amino]-propionic acid |
| 15 | 3-[(7-tert-Butyl-2-hydroxy-4-oxo-5,6,7,8-tetrahydro-4H-9-thia-1,4a-diaza-fluorene-3-carbonyl)-amino]-propionic acid |
| 16 | {[7-(4-Fluoro-benzoyl)-2-hydroxy-4-oxo-5,6,7,8-tetrahydro-4H-9-thia-1,4a,7-triaza-fluorene-3-carbonyl]-amino}-acetic acid |
| 17 | {[7-(5-Chloro-thiophene-2-sulfonyl)-2-hydroxy-4-oxo-5,6,7,8-tetrahydro-4H-9-thia-1,4a,7-triaza-fluorene-3-carbonyl]-amino}-acetic acid |
| 18 | {[2-Hydroxy-4-oxo-7-(5-trifluoromethyl-pyridin-2-yl)-5,6,7,8-tetrahydro-4H-9-thia-1,4a,7-triaza-fluorene-3-carbonyl]-amino}-acetic acid |
| 19 | {[2-Hydroxy-4-oxo-7-(4-trifluoromethoxy-benzenesulfonyl)-5,6,7,8-tetrahydro-4H-9-thia-1,4a,7-triaza-fluorene-3-carbonyl]-amino}-acetic acid |
| 20 | {[7-(2,2-Dimethyl-propionyl)-2-hydroxy-4-oxo-5,6,7,8-tetrahydro-4H-9-thia-1,4a,7-triaza-fluorene-3-carbonyl]-amino}-acetic acid |
| 21 | {[7-(4-Butyl-benzoyl)-2-hydroxy-4-oxo-5,6,7,8-tetrahydro-4H-9-thia-1,4a,7-triaza-fluorene-3-carbonyl]-amino}-acetic acid |
| 22 | {[2-Hydroxy-4-oxo-7-(4-trifluoromethoxy-benzoyl)-5,6,7,8-tetrahydro-4H-9-thia-1,4a,7-triaza-fluorene-3-carbonyl]-amino}-acetic acid |
| 23 | {[7-(4-Chloro-benzyl)-2-hydroxy-4-oxo-5,6,7,8-tetrahydro-4H-9-thia-1,4a,7-triaza-fluorene-3-carbonyl]-amino}-acetic acid |
| 24 | {[7-(4-Fluoro-phenylthiocarbamoyl)-2-hydroxy-4-oxo-5,6,7,8-tetrahydro-4H-9-thia-1,4a,7-triaza-fluorene-3-carbonyl]-amino}-acetic acid |
| 25 | [(2-Hydroxy-7-isopropylthiocarbamoyl-4-oxo-5,6,7,8-tetrahydro-4H-9-thia-1,4a,7-triaza-fluorene-3-carbonyl)-amino]-acetic acid |
| 26 | 3-(Carboxymethyl-carbamoyl)-2-hydroxy-4-oxo-5,8-dihydro-4H,6H-9-thia-1,4a,7-triaza-fluorene-7-carboxylic acid benzyl ester |
| 27 | {[7-(2-Cyclopropyl-acetyl)-2-hydroxy-4-oxo-5,6,7,8-tetrahydro-4H-9-thia-1,4a,7-triaza-fluorene-3-carbonyl]-amino}-acetic acid |
| 28 | ({7-[2-(4-Chloro-phenyl)-acetyl]-2-hydroxy-4-oxo-5,6,7,8-tetrahydro-4H-9-thia-1,4a,7-triaza-fluorene-3-carbonyl}-amino)-acetic acid |
| 29 | {[7-(2-Cyclopentyl-acetyl)-2-hydroxy-4-oxo-5,6,7,8-tetrahydro-4H-9-thia-1,4a,7-triaza-fluorene-3-carbonyl]-amino}-acetic acid |
| 30 | 3-[(2-Hydroxy-4-oxo-6,7,8,9-tetrahydro-4H,5H-10-thia-1,4a-diaza-benzo[a]azulene-3-carbonyl)-amino]-propionic acid |
| 31 | {[2-Hydroxy-7-(4-methoxy-benzyl)-4-oxo-5,6,7,8-tetrahydro-4H-9-thia-1,4a,7-triaza-fluorene-3-carbonyl]-amino}-acetic acid |
| 32 | 2-[(2-Hydroxy-4-oxo-6,7,8,9-tetrahydro-4H,5H-10-thia-1,4a-diaza-benzo[a]azulene-3-carbonyl)-amino]-propionic acid |
| 33 | {[7-(6-Chloro-pyridine-3-carbonyl)-2-hydroxy-4-oxo-5,6,7,8-tetrahydro-4H-9-thia-1,4a,7-triaza-fluorene-3-carbonyl]-amino}-acetic acid |
| 34 | [(2-Hydroxy-7,7-dimethyl-4-oxo-5,6,7,8-tetrahydro-4H-9-thia-1,4a-diaza-fluorene-3-carbonyl)-amino]-acetic acid |
| 35 | {[7-(6-Chloro-pyridazin-3-yl)-2-hydroxy-4-oxo-5,6,7,8-tetrahydro-4H-9-thia-1,4a,7-triaza-fluorene-3-carbonyl]-amino}-acetic acid |
| 36 | {[7-(3-Cyano-pyridin-2-yl)-2-hydroxy-4-oxo-5,6,7,8-tetrahydro-4H-9-thia-1,4a,7-triaza-fluorene-3-carbonyl]-amino}-acetic acid |
| 37 | {[7-(3-Chloro-4-methoxy-benzoyl)-2-hydroxy-4-oxo-5,6,7,8-tetrahydro-4H-9-thia-1,4a,7-triaza-fluorene-3-carbonyl]-amino}-acetic acid |
| 38 | [(2-Hydroxy-4-oxo-5,6,7,8,9,10-hexahydro-4H-11-thia-1,4a-diaza-cycloocta[a]indene-3-carbonyl)-amino]-acetic acid |
| 39 | [(2-Hydroxy-7-indan-5-ylmethyl-4-oxo-5,6,7,8-tetrahydro-4H-9-thia-1,4a,7-triaza-fluorene-3-carbonyl)-amino]-acetic acid |
| 40 | 2-[(2-Hydroxy-7,7-dimethyl-4-oxo-5,6,7,8-tetrahydro-4H-9-thia-1,4a-diaza-fluorene-3-carbonyl)-amino]-propionic acid |
| 41 | {[7-(3,5-Dimethoxy-benzoyl)-2-hydroxy-4-oxo-5,6,7,8-tetrahydro-4H-9-thia-1,4a,7-triaza-fluorene-3-carbonyl]-amino}-acetic acid |
| 42 | {[2-Hydroxy-7-(4-methanesulfonyl-benzoyl)-4-oxo-5,6,7,8-tetrahydro-4H-9-thia-1,4a,7-triaza-fluorene-3-carbonyl]-amino}-acetic acid |
| 43 | 2-[(2-Hydroxy-7,7-dimethyl-4-oxo-5,6,7,8-tetrahydro-4H-9-thia-1,4a-diaza-fluorene-3-carbonyl)-amino]-3-methyl-butyric acid (L-isomer) |
| 44 | 2-[(2-Hydroxy-7,7-dimethyl-4-oxo-5,6,7,8-tetrahydro-4H-9-thia-1,4a-diaza-fluorene-3-carbonyl)-amino]-propionic acid (D-isomer) |
| 45 | {[7-(3,5-Dichloro-4-methoxy-benzoyl)-2-hydroxy-4-oxo-5,6,7,8-tetrahydro-4H-9-thia-1,4a,7-triaza-fluorene-3-carbonyl]-amino}-acetic acid |
| 46 | {[7-(3,5-Bis-trifluoromethyl-benzyl)-2-hydroxy-4-oxo-5,6,7,8-tetrahydro-4H-9-thia-1,4a,7-triaza-fluorene-3-carbonyl]-amino}-acetic acid |

| Compd. No. | Chemical Name |
|---|---|
| 47 | {[2-Hydroxy-4-oxo-7-(4-propyl-benzoyl)-5,6,7,8-tetrahydro-4H-9-thia-1,4a,7-triaza-fluorene-3-carbonyl]-amino}-acetic acid |
| 48 | {[7-(3,5-Bis-trifluoromethyl-benzoyl)-2-hydroxy-4-oxo-5,6,7,8-tetrahydro-4H-9-thia-1,4a,7-triaza-fluorene-3-carbonyl]-amino}-acetic acid |
| 49 | {[7-(3,4-Dichloro-benzyl)-2-hydroxy-4-oxo-5,6,7,8-tetrahydro-4H-9-thia-1,4a,7-triaza-fluorene-3-carbonyl]-amino}-acetic acid |
| 50 | [(2-Hydroxy-4-oxo-5,6,7,8-tetrahydro-4H-9-thia-1,4a,7-triaza-fluorene-3-carbonyl)-amino]-acetic acid, hydrochloride salt |
| 51 | {[2-Hydroxy-7-(7-methoxy-6-methyl-indan-4-ylmethyl)-4-oxo-5,6,7,8-tetrahydro-4H-9-thia-1,4a,7-triaza-fluorene-3-carbonyl]-amino}-acetic acid |
| 52 | {[2-Hydroxy-4-oxo-7-(4-trifluoromethyl-benzyl)-5,6,7,8-tetrahydro-4H-9-thia-1,4a,7-triaza-fluorene-3-carbonyl]-amino}-acetic acid |
| 53 | [(7,7-Diethyl-2-hydroxy-4-oxo-5,6,7,8-tetrahydro-4H-9-thia-1,4a-diaza-fluorene-3-carbonyl)-amino]-acetic acid |
| 54 | 2-[(2-Hydroxy-7,7-dimethyl-4-oxo-5,6,7,8-tetrahydro-4H-9-thia-1,4a-diaza-fluorene-3-carbonyl)-amino]-2-methyl-propionic acid |
| 55 | [(2-Hydroxy-7,7-dimethyl-4-oxo-5,6,7,8-tetrahydro-4H-9-thia-1,4a-diaza-fluorene-3-carbonyl)-amino]-phenyl-acetic acid, L-isomer |
| 56 | [(7-Benzoylamino-2-hydroxy-4-oxo-5,6,7,8-tetrahydro-4H-9-thia-1,4a-diaza-fluorene-3-carbonyl)-amino]-acetic acid |
| 57 | [(2-Hydroxy-4-oxo-5,6,7,8-tetrahydro-4H-9-oxa-1,4a-diaza-fluorene-3-carbonyl)-amino]-acetic acid |
| 58 | [(2-Hydroxy-7-methyl-4-oxo-5,6,7,8-tetrahydro-4H-9-thia-1,4a-diaza-fluorene-3-carbonyl)-amino]-acetic acid |
| 59 | [(2-Hydroxy-4-oxo-7-propyl-5,6,7,8-tetrahydro-4H-9-thia-1,4a-diaza-fluorene-3-carbonyl)-amino]-acetic acid |
| 60 | [(2-Hydroxy-6,6-dimethyl-4-oxo-5,6,7,8-tetrahydro-4H-9-thia-1,4a-diaza-fluorene-3-carbonyl)-amino]-acetic acid |
| 61 | [(2-Hydroxy-7,7-dimethyl-4-oxo-5,6,7,8-tetrahydro-4H-9-thia-1,4a-diaza-fluorene-3-carbonyl)-methyl-amino]-acetic acid |
| 62 | 1-[(2-Hydroxy-7,7-dimethyl-4-oxo-5,6,7,8-tetrahydro-4H-9-thia-1,4a-diaza-fluorene-3-carbonyl)-amino]-cyclohexanecarboxylic acid |
| 63 | 1-(7,7-Dimethyl-2-methylsulfanyl-4-oxo-5,6,7,8-tetrahydro-4H-9-thia-1,4a-diaza-fluorene-3-carbonyl)-piperidine-4-carboxylic acid |
| 64 | [(2-Hydroxy-4-oxo-7-phenyl-5,6,7,8-tetrahydro-4H-9-thia-1,4a-diaza-fluorene-3-carbonyl)-amino]-acetic acid |
| 65 | [(2-Hydroxy-4-oxo-5,8-dihydro-4H,6H-7-oxa-9-thia-1,4a-diaza-fluorene-3-carbonyl)-amino]-acetic acid |
| 66 | [(2-Hydroxy-5,7,7-trimethyl-4-oxo-5,6,7,8-tetrahydro-4H-9-thia-1,4a-diaza-fluorene-3-carbonyl)-amino]-acetic acid |
| 67 | [(2-Hydroxy-4,7,7-trioxo-5,6,7,8-tetrahydro-4H-7lambda*6*,9-dithia-1,4a-diaza-fluorene-3-carbonyl)-amino]-acetic acid |
| 68 | [(2-Methylsulfanyl-4-oxo-5,8-dihydro-4H,6H-7,9-dithia-1,4a-diaza-fluorene-3-carbonyl)-amino]-acetic acid |
| 69 | [(5-Ethoxy-2-methylsulfanyl-4-oxo-5,6,7,8-tetrahydro-4H-9-thia-1,4a-diaza-fluorene-3-carbonyl)-amino]-acetic acid ethyl ester |
| 70 | N-[(2'-hydroxy-4'-oxo-6',9'-dihydro-4'H,7'H-spiro[cyclopropane-1,8'-pyrimido[2,1-b][1,3]benzothiazol]-3'-yl)carbonyl]glycine |
| 71 | [(7-Isopropyl-2-methylsulfanyl-4-oxo-5,6,7,8-tetrahydro-4H-9-thia-1,4a,7-triaza-fluorene-3-carbonyl)-amino]-acetic acid |
| 72 | 3-(Carboxymethyl-carbamoyl)-2-hydroxy-4-oxo-5,6,7,8-tetrahydro-4H-9-thia-1,4a-diaza-fluorene-7-carboxylic acid |
| 73 | {[7-(3,5-Dimethyl-pyrazol-1-yl)-2-methylsulfanyl-4-oxo-5,6,7,8-tetrahydro-4H-9-thia-1,4a-diaza-fluorene-3-carbonyl]-amino}-acetic acid |
| 74 | 2-[(2-Hydroxy-4-oxo-5,6,7,8-tetrahydro-4H-9-thia-1,4a-diaza-fluorene-3-carbonyl)-amino]-3-methyl-pentanoic acid (L-isomer) |
| 75 | 3-(1H-Indol-2-yl)-2-[(2-methylsulfanyl-4-oxo-5,6,7,8-tetrahydro-4H-9-thia-1,4a-diaza-fluorene-3-carbonyl)-amino]-propionic acid (L-isomer) |
| 76 | 3-(3H-Imidazol-4-yl)-2-[(2-methylsulfanyl-4-oxo-5,6,7,8-tetrahydro-4H-9-thia-1,4a-diaza-fluorene-3-carbonyl)-amino]-propionic acid (L-isomer) |
| 77 | 3-(4-Hydroxy-phenyl)-2-[(2-methylsulfanyl-4-oxo-5,6,7,8-tetrahydro-4H-9-thia-1,4a-diaza-fluorene-3-carbonyl)-amino]-propionic acid (L-isomer) |
| 78 | [(2-Hydroxy-4-oxo-7-pyridin-4-ylmethyl-5,6,7,8-tetrahydro-4H-9-thia-1,4a,7-triaza-fluorene-3-carbonyl)-amino]-acetic acid |
| 79 | 2-Methylsulfanyl-4-oxo-6,7,8,9-tetrahydro-4H,5H-10-thia-1,4a-diaza-benzo[a]azulene-3-carboxylic acid (2-oxo-2-pyrrolidin-1-yl-ethyl)-amide |
| 80 | [(2-Hydroxy-7,7-dimethyl-4-oxo-5,6,7,8-tetrahydro-4H-9-thia-1,4a-diaza-fluorene-3-carbonyl)-amino]-acetic acid, Disodium salt |
| 81 | [(2-Ethoxy-4-oxo-6,7,8,9-tetrahydro-4H,5H-10-thia-1,4a-diaza-benzo[a]azulene-3-carbonyl)-amino]-acetic acid |
| 82 | [(2-Hydroxy-4-oxo-6,7,8,9-tetrahydro-4H,5H-10-thia-1,4a-diaza-benzo[a]azulene-3-carbonyl)-amino]-acetic acid, Disodium salt |
| 83 | [(2-Hydroxy-4-oxo-6,7,8,9-tetrahydro-4H,5H-10-thia-1,4a-diaza-benzo[a]azulene-3-carbonyl)-amino]-acetic acid, arginine salt (2:1) |
| 84 | [(2-Hydroxy-4-oxo-6,7,8,9-tetrahydro-4H,5H-10-thia-1,4a-diaza-benzo[a]azulene-3-carbonyl)-amino]-acetic acid, lysine salt |

-continued

| Compd. No. | Chemical Name |
|---|---|
| 85 | [(2-Hydroxy-4-oxo-6,7,8,9-tetrahydro-4H,5H-10-thia-1,4a-diaza-benzo[a]azulene-3-carbonyl)-amino]-acetic acid, dipotassium salt |
| 86 | [(2-Hydroxy-4-oxo-6,7,8,9-tetrahydro-4H,5H-10-thia-1,4a-diaza-benzo[a]azulene-3-carbonyl)-amino]-acetic acid, calcium salt (2:1) |
| 87 | [(2-Hydroxy-4-oxo-6,7,8,9-tetrahydro-4H,5H-10-thia-1,4a-diaza-benzo[a]azulene-3-carbonyl)-amino]-acetic acid, magnesium salt (2:1) |
| 88 | [(2-Hydroxy-4-oxo-6,7,8,9-tetrahydro-4H,5H-10-thia-1,4a-diaza-benzo[a]azulene-3-carbonyl)-amino]-acetic acid, ammonium salt |
| 89 | [(2-Hydroxy-4-oxo-6,7,8,9-tetrahydro-4H,5H-10-thia-1,4a-diaza-benzo[a]azulene-3-carbonyl)-amino]-acetic acid, diethylamine salt |
| 90 | [(2-Hydroxy-4-oxo-6,7,8,9-tetrahydro-4H,5H-10-thia-1,4a-diaza-benzo[a]azulene-3-carbonyl)-amino]-acetic acid, choline salt |
| 91 | [(2-Hydroxy-4-oxo-6,7,8,9-tetrahydro-4H,5H-10-thia-1,4a-diaza-benzo[a]azulene-3-carbonyl)-amino]-acetic acid, tromethamine salt |
| 92 | [(2-Hydroxy-4-oxo-6,7,8,9-tetrahydro-4H,5H-10-thia-1,4a-diaza-benzo[a]azulene-3-carbonyl)-amino]-acetic acid, histidine salt |
| 83 | 2-Methylsulfanyl-4-oxo-6,7,8,9-tetrahydro-4H,5H-10-thia-1,4a-diaza-benzo[a]azulene-3-carboxylic acid carbamoylmethyl-amide |
| 84 | 2-Methylsulfanyl-4-oxo-6,7,8,9-tetrahydro-4H,5H-10-thia-1,4a-diaza-benzo[a]azulene-3-carboxylic acid hydroxycarbamoylmethyl-amide |
| 85 | [(4-Chloro-benzyl)-(2-methylsulfanyl-4-oxo-6,7,8,9-tetrahydro-4H,5H-10-thia-1,4a-diaza-benzo[a]azulene-3-carbonyl)-amino]-acetic acid |
| 86 | 4-[Cyclopentyl-(2-methylsulfanyl-4-oxo-6,7,8,9-tetrahydro-4H,5H-10-thia-1,4a-diaza-benzo[a]azulene-3-carbonyl)-amino]-butyric acid |
| 97 | 2-Hydroxy-4-oxo-6,7,8,9-tetrahydro-4H,5H-10-thia-1,4a-diaza-benzo[a]azulene-3-carboxylic acid (2-oxo-2-pyrrolidin-1-yl-ethyl)-amide |
| 98 | 2-Hydroxy-4-oxo-6,7,8,9-tetrahydro-4H,5H-10-thia-1,4a-diaza-benzo[a]azulene-3-carboxylic acid cyclohexylcarbamoylmethyl-amide |
| 99 | 2-Hydroxy-4-oxo-6,7,8,9-tetrahydro-4H,5H-10-thia-1,4a-diaza-benzo[a]azulene-3-carboxylic acid (benzylcarbamoyl-methyl)-amide |
| 100 | 4-[Cyclopentyl-(2-hydroxy-4-oxo-6,7,8,9-tetrahydro-4H,5H-10-thia-1,4a-diaza-benzo[a]azulene-3-carbonyl)-amino]-butyric acid |
| 101 | [Benzyl-(2-hydroxy-4-oxo-6,7,8,9-tetrahydro-4H,5H-10-thia-1,4a-diaza-benzo[a]azulene-3-carbonyl)-amino]-acetic acid |

Definitions

The following definitions apply to the terms as used throughout this specification, unless otherwise limited in specific instances:

The term "compound" employed herein refers to any compound encompassed by the generic formula disclosed herein. The compounds described herein may contain one or more double bonds and therefore, may exist as isomers, stereoisomers, such as geometric isomers, E and Z isomers, and may possess asymmetric carbon atoms (optical centres) and therefore may exist as enantiomers, diastereoisomers. Accordingly, the chemical structures described herein encompasses all possible stereoisomers of the illustrated compounds including the stereoisomerically pure form (e.g., geometrically pure) and stereoisomeric mixtures (racemates). The compound described herein, may exist as a conformational isomers such as chair or boat form. The compounds may also exist in several tautomeric forms including the enol form, the keto form and mixtures thereof. Accordingly, the chemical structures described herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to $^2$H, $^3$H, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The use of the terms "a" and "an" and "the" and similar referents in the context of describing the invention (especially in the context of the following claims) are to be construed to cover both the singular and the plural, unless otherwise indicated herein or clearly contradicted by context.

Further, it should be understood, when partial structures of the compounds are illustrated, a dash ("-") indicate the point of attachment of the partial structure to the rest of the molecule.

The nomenclature of the compounds of the present invention as indicated herein is according to ISIS® draw (version 2.2) from MDL & ACD/Labs Pro-version 12.0.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, carbonic acid, phosphoric acid, and the like; or formed with organic acids such as acetic acid, propionic acid, isobutyric acid, hexanoic acid, cyclopentanepropionic acid, oxalic acid, glycolic acid, pyruvic acid, lactic acid, malonic acid, succinic acid, suberic acid, malic acid, maleic acid, fumaric acid, tartaric acid, citric acid, benzoic acid, 3-(4-hydroxybenzoyl) benzoic acid, phthalic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glucuronic acid, galactunoric acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. Also included are salts of amino acids such as arginate and the like (see, for example, Berge, S. M., et al., "Pharmaceutical Salts", Journal of Pharmaceutical Science, 1977, 66, 1-19).

As used herein, the term "polymorph" pertains to compounds having the same chemical formula, the same salt type and having the same form of hydrate/solvate but having different crystallographic properties.

As used herein, the term "hydrate" pertains to a compound having a number of water molecules bonded to the compound.

As used herein, the term "solvate" pertains to a compound having a number of solvent molecules bonded to the compound.

The present invention also encompasses compounds which are in a prodrug form. Prodrugs of the compounds described herein are those compounds that readily undergo chemical changes under physiological conditions (in vivo) to provide the compounds of the present invention. Additionally, prodrugs can be converted to the compounds of the present invention by chemical or biochemical methods in an ex vivo environment, for example, transdermal patch reservoir with a suitable enzyme or chemical. Prodrugs are, in some situation, easier to administer than the parent drug. They may, for instance, be bioavailable by oral administration whereas the parent drug is not. The prodrug may also have improved solubility in pharmacological composition over the parent drug. Esters, peptidyl derivatives and the like, of the compounds are the examples of prodrugs of the present invention. In vivo hydrolysable (or cleavable) ester of a compound of the present invention that contains a carboxy group is, for example, a pharmaceutically acceptable ester which is hydrolysed in the human or animal body to produce the parent acid.

The term "substituted", as used herein, includes mono- and poly-substitution by a named substituent to the extent such single and multiple substitution (including multiple substitution at the same site) is chemically allowed and which means that any one or more hydrogens on the designated atom is replaced with a selection from the indicated group, provided that the designated atom's normal valence is not exceeded, and that the substitution results in a stable compound, for example, when a substituent is keto, then the two hydrogens on the atom are replaced. All substituents (R, $R_1$, $R_2$ . . . ) and their further substituents described herein may be attached to the main structure at any heteroatom or carbon atom which results in formation of stable compound.

As used herein, a "halo" or "halogen" substituent is a monovalent halogen radical chosen from chloro, bromo, iodo and fluoro.

The term "alkyl" used either alone or in attachment with another group refers to a saturated aliphatic hydrocarbon radical having the indicated number of carbon atoms and that is unsubstituted or substituted. When a subscript is used with reference to an alkyl, the subscript refers to the number of carbon atoms that group may contain. For example, a "$C_1$-$C_6$" would refer to any alkyl group containing one to six carbons in the structure. Alkyl may be straight chain, branched chain or cyclic. The said alkyl may be optionally substituted with substituents at positions that do not significantly interfere with the preparation of compounds falling within the scope of this invention. The said alkyl is optionally substituted with one to two substituents independently selected from the group consisting of $C_{1-3}$alkoxy, amino, mono($C_{1-3}$alkyl)amino, di($C_{1-3}$alkyl)amino, $C_{1-3}$alkyl, and hydroxy.

The term "alkoxy" refers to any alkyl group as defined herein above attached to the parent molecular moiety through an oxygen breidge.

The term "aryl" refers to an aromatic group for example, which is a 6 to 10 membered monocyclic or bicyclic carbon-containing ring system, which may be unsubstituted or substituted.

The term "heteroaryl" refers to an aromatic group for example, which is a 5 to 14 membered monocyclic or bicyclic ring system, which has at least one heteroatom, which may be unsubstituted or substituted. The term "heteroatom" as used herein includes oxygen, sulfur and nitrogen.

The term "heterocyclyl" refers to a fully or partially saturated cyclic group, for example, which is a 3 to 14 membered monocyclic or bicyclic ring system, which has at least one heteroatom, which may be unsubstituted or substituted. The term "heteroatom" as used herein includes oxygen, sulfur and nitrogen.

As used herein, "room temperature" refers to a temperature between 25° C. and 35° C.

As used herein, the term "mammal" means a human or an animal such as monkeys, primates, dogs, cats, horses, cows, etc.

The terms "treating" or "treatment" of any disease or disorder as used herein to mean administering a compound to a mammal in need thereof.

The phrase "a therapeutically effective amount" means the amount of a compound that, when administered to a patient for treating a disease, is sufficient to effect such treatment for the disease. The "therapeutically effective amount" will vary depending on the compound, mode of administration, the disease and its severity and the age, weight, etc., of the patient to be treated.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

It has been surprisingly found that partially saturated tricyclic compounds containing one or more heteroatom exhibits better in-vitro activity profile.

In another embodiment, present invention provides the process for preparing the compounds of formula (I).

The following reaction schemes are given to disclose the synthesis of the compounds according to the present invention.

Accordingly, the compounds of formula (I) of the present invention may be prepared as described in the schemes below.

Formula (I) includes, but is not limited to, compounds of formula (Ia), (Ib), (Ic), (Id), (Ie) (If), (Ig), (Ih), (Ii), (Ij) and (Ik); compound of formula (Ia) includes, but is not limited to, compounds of formula (Ia-1) and (Ia-2); compound of formula (Ic) includes, but is not limited to, compounds of formula (Ic-1), (Ic-2) and (Ic-3); compound of formula (Id) include, but is not limited to, compounds of formula (Id-1) and (Id-2).

The compound of formula (Ia-Ik), which belongs to general formula (I), can be prepared by the following methods described in schemes A, B, C, D & E.

Scheme A
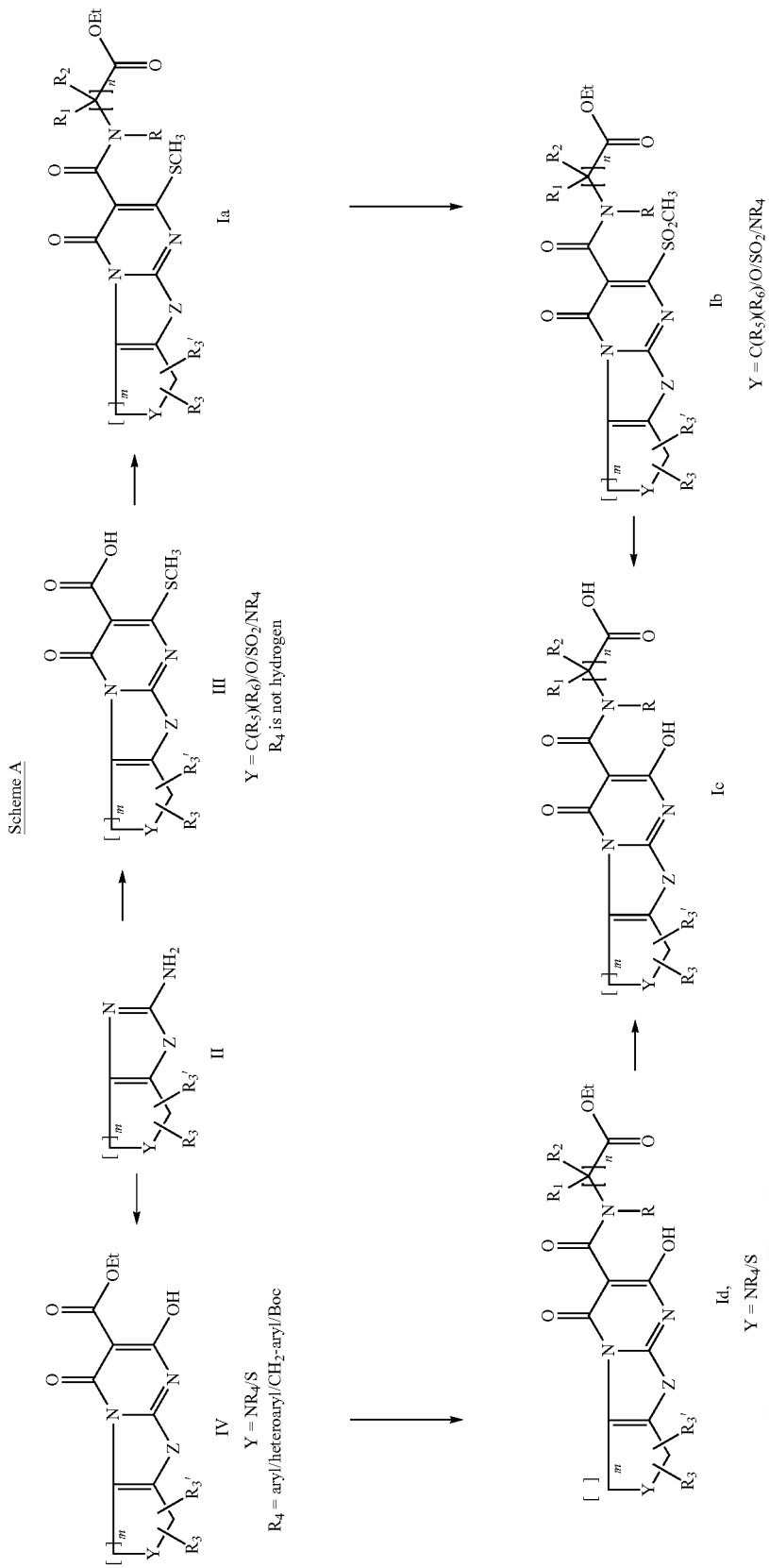

Compounds belong to general formula (I) such as compound of formula (Ia), (Ib), (Ic) and (Id), can be synthesized from the compound of formula (III) and (IV) as shown in scheme A, wherein R, $R_1$, $R_2$, $R_3$, $R_3'$, Z, m and n are as defined above while Y and $R_4$ are defined in scheme A.

In general, the compound of formula (Ia) can be prepared by reacting the compound of formula (III) with various amino esters having the following general formula,

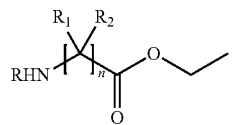

wherein, n, R, $R_1$, $R_2$ are as defined as above, using suitable coupling reagent such as carbodiimides, CDI (1,1'-Carbonyldiimidazole) or PyBop (benzotriazol-1-yl-oxytripyrrolidinophosphonium hexafluorophosphate) in the presence of base like tertiary amine such as triethylamine and in aprotic solvent such as tetrahydrofuran, dichloromethane etc.

The compound of formula (Ib) can be prepared by the oxidation of compounds of formula (Ia) with suitable oxidizing reagent such as peracid or hydrogen peroxide in solvent like dioxan, tetrahydrofuran or dichloromethane at room temperature for 2-6 hrs. The compound of formula (Ib), upon alkaline hydrolysis in the presence of base including alkali hydroxide such as sodium hydroxide and in inert solvent like tetrahydrofuran, water or mixture thereof, provides compound of formula (Ic).

The compound of formula (III) can be prepared by heating appropriate amines of formula (II) with 5-(bis-ethylsulfanylmethylene)-2,2-dimethyl-[1,3]dioxane-4,6-dione in suitable solvent such as alcoholic solvent or dimethylformamide at 80-85° C. for 2-24 hrs.

The compound of formula (Id) can be prepared by reacting the compound of formula (IV) with various amino esters having the following general formula,

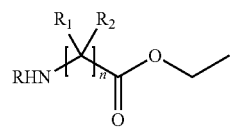

wherein, n, R, $R_1$, $R_2$ are as defined as above, in suitable solvent and base such as pyridine at 100-110° C. for 2 to 6 hrs.

The compound of formula (Ic) can also be prepared by alkaline hydrolysis of compound of formula (Id) in the presence of base including alkali hydroxide such as sodium hydroxide and in inert solvent like tetrahydrofuran, water or mixture thereof.

The compound of formula (IV) can be prepared by reacting the appropriate amines of formula (II) with triethyl methantricarboxylate in suitable solvent such as xylene, toluene or bromobenzene at elevated temperature.

The compound of formula (II) such as thiazole-2-amines (Z is S) or oxazole-2-amines (Z is O) is either synthesized using method described in literature (US 2006/0252837, U.S. Pat. No. 4,423,048 and J. Med. Chemistry, 2002, 45(23), 5090-5097) or commercially available.

Scheme B

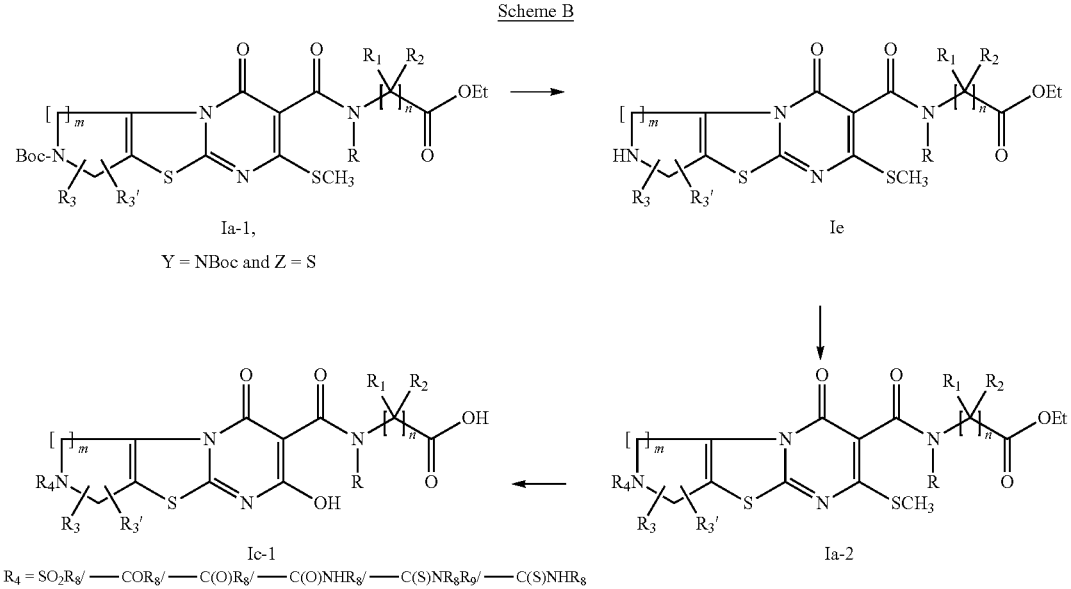

Several N-unsubstituted and N-substituted derivatives belongs to formula (I), such as compounds of formula (Ie), (Ia-2) and (Ic-1) can be prepared from the compound of formula (Ia-1), as shown in scheme B, wherein R, $R_1$, $R_2$, $R_3$, $R_3'$, $R_4$, $R_8$, $R_9$, m and n are as defined above.

The compound of formula (Ic-1) can be prepared by oxidation of compounds of formula (Ia-2) with peracid or hydrogen peroxide in solvent like tetrahydrofuran or dichloromethane at room temperature for 2-6 hrs, followed by basic hydrolysis in the presence of base including alkali hydroxide such as sodium hydroxide and in inert solvent like tetrahydrofuran, water or mixture thereof at room temperature for 2-6 hrs.

The compound of formula (Ia-2) can be prepared by introducing various $R_4$ groups in compound of formula (Ie), by reacting it with suitable reagents such as sulfonyl chlorides, carbonyl chlorides, chloroformates, isocyanates, carbamoyl chlorides, isothiocyanates and carbamothioic chloride in the presence of organic base such as triethylamine, pyridine or N-methylmorpholine and in solvent like tetrahydrofuran, dichloromethane or mixture thereof at room temperature for 2-8 hrs.

The compound of formula (Ie) can be prepared by the deprotection of Boc group in compounds of formula (Ia-1) using acidic reagent like trifluoroacetic acid in inert solvent like tetrahydrofuran or dichloromethane at room temperature for 2-6 hrs.

The compound of formula (Ia-1) can be prepared from compound of formula (III) as described in Scheme-A.

The compound of formula (Ic-3) can be prepared by alkaline hydrolysis of compounds of formula (Id-2) in the presence of base including alkali hydroxide such as sodium hydroxide and in inert solvent like tetrahydrofuran, water or mixture thereof at room temperature for 2-6 hrs.

The compound of formula (Id-2) can be prepared by introducing various $R_4$ group at nitrogen of compounds of formula (If) by reacting with $R_4$-Halo, wherein $R_4$ is —$CH_2$-aryl, in the presence of suitable base like triethylamine, pyridine or N-methylmorpholine and solvent such as dichloromethane or tetrahydrofuran at room temperature for 5-12 hrs.

The compounds of formula (If) can be obtained by the esterification of compounds of formula (Ic-2) with ethanol in the presence of carbodiimide followed by removal of Boc

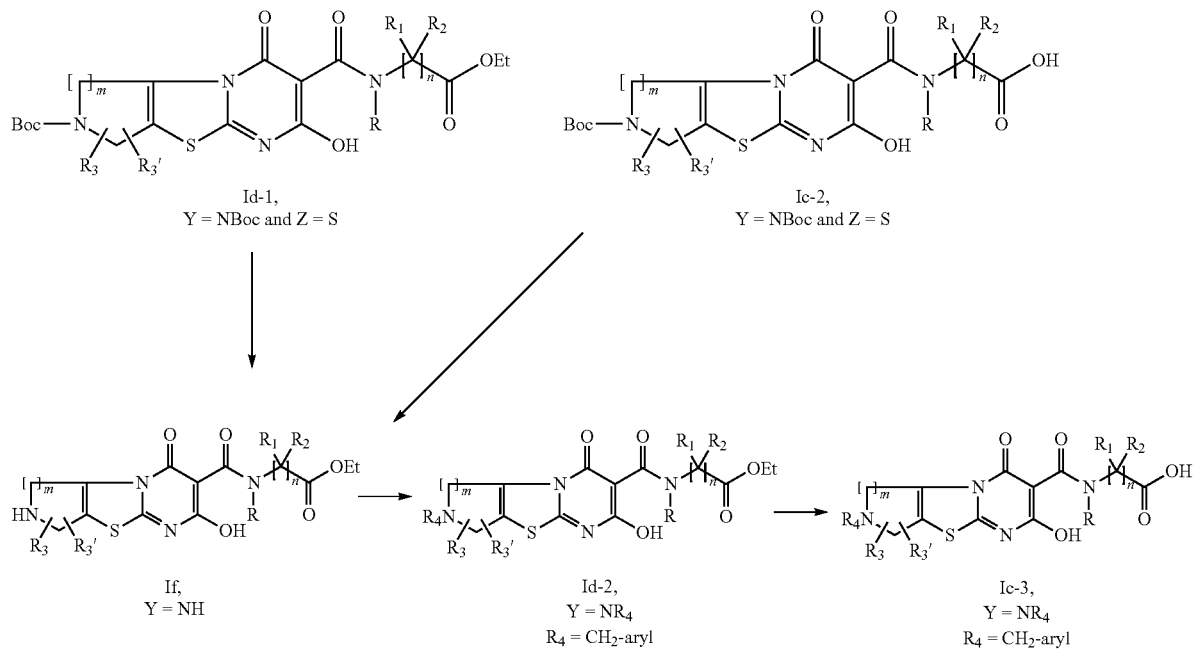

Scheme C

In an alternate way, various N-unsubstituted and N-substituted derivatives belongs to formula (I), such as compounds of formula (If), (Id-2) and (Ic-3) can be prepared from the compound of formula (Id-1) or (Ic-2), as shown in scheme C. wherein R, $R_1$, $R_2$, $R_3$, $R_{3'}$, $R_4$, m and n are as defined above.

group using acidic reagent like trifluoroacetic acid in an inert solvent like tetrahydrofuran or dichloromethane.

In an alternate way, the compound of formula (If) can be prepared by the Boc deprotection of compounds of formula (Id-1) using similar conditions as described in scheme-B.

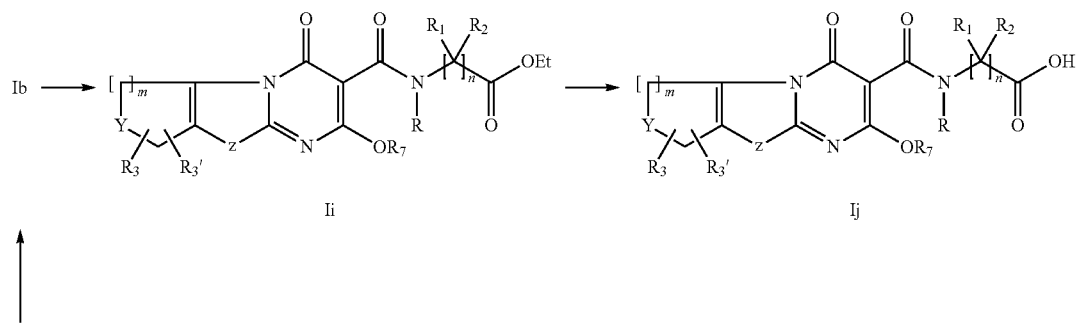

Scheme D

Ia ⟶ 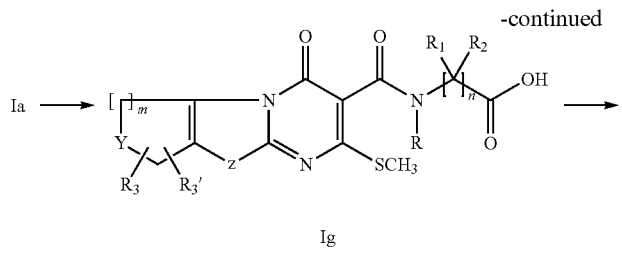 ⟶ 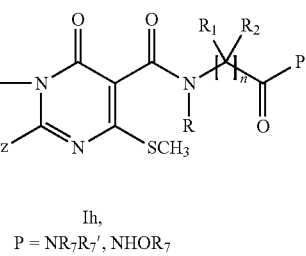

Ig

Ih,
P = NR$_7$R$_7$', NHOR$_7$

Various compounds of formula (I) such as compounds of formula (Ig), (Ih) (Ii) and (Ij) can be prepared from the compound of formula (Ia) or (Ib), as shown in scheme D, wherein R, R$_1$, R$_2$, R$_3$, R$_3$', R$_7$, R$_7$', Y, z, m and n are as defined above.

The compound of formula (Ih) can be prepared by reacting the compound of formula (Ig) with appropriate amine using coupling reagent such as carbodiimides, CDI or PyBop.

The compound of formula (Ij) can be prepared by alkaline hydrolysis of compound of formula (II) in the presence of base including alkali hydroxide such as sodium hydroxide and in inert solvent like tetrahydrofuran, water or mixture thereof.

The compound of formula (II) can be obtained by reacting compounds of formula (Ib) with sodium alkoxide such as sodium ethoxide in suitable solvent such as tetrahydrofuran at room temperature.

The compound of formula (Ig) can be prepared by alkaline hydrolysis of the compound of formula (Ia).

Scheme E

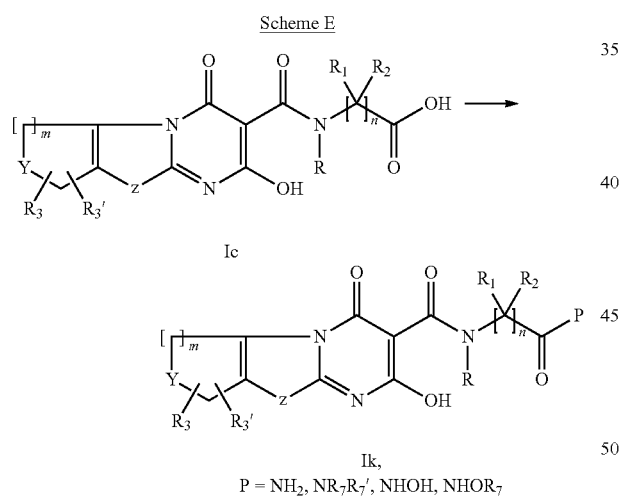

Ik,
P = NH$_2$, NR$_7$R$_7$', NHOH, NHOR$_7$

Various compounds of formula (I), such as compounds of formula (Ik) can be prepared as shown in scheme E, wherein R, R$_1$, R$_2$, R$_3$, R$_3$', Y, z, m and n are as defined above. The compounds belong to formula (Ik), where P is —NH$_2$, —NHR$_7$, —NR$_7$R$_7$', NHOH and NHOR$_7$ can be obtained by coupling of formula (Ic) with appropriate amine in suitable condition such as using coupling reagent such as carbodiimides in suitable aprotic solvent.

Further, compounds belong to formula (I), where P is NHSO$_2$R$_7$ and NHCOR$_7$ can be obtained by coupling of formula (IV) or (III) or (Ic) with suitable reagents and conditions.

A general synthetic method is provided for each of the disclosed groups of chemical compounds. One of ordinary skill will recognize to substitute appropriately modified starting material containing the various substituents. One of ordinary skill will readily synthesize the disclosed compounds according to the present invention using conventional synthetic organic techniques and microwave techniques from starting material which are either purchased or may be readily prepared using prior art methods.

The compounds of the present invention may have chiral centers and occur as racemates, racemic mixtures and as individual diastereomers or enantiomers with all isomeric forms being included in the present invention. Therefore, where a compound is chiral, the separate enantiomers, substantially free of the other, are included within the scope of the invention; further included are all mixtures of the two enantiomers.

The novel compounds of the present invention are not, however, to be construed as forming the only genus that is considered as the invention, and any combination of the compounds or their moieties may itself form a genus.

The novel compounds of the present invention were prepared according to the procedure of the schemes as described herein above, using appropriate materials and are further exemplified by the following specific examples. The examples are not to be considered nor construed as limiting the scope of the invention set forth.

EXAMPLES

Example-1

Preparation of [(2-hydroxy-4-oxo-5,6,7,8-tetrahydro-4H-9-thia-1,4a-diaza-fluorene-3-carbonyl)-amino]-acetic acid (Compound no. 1)

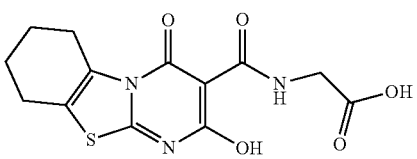 [SMILES: O=C(O)CNC(=O)c1c(O)nc2sc3c(n2c1=O)CCCC3]

Step-1: Synthesis of 2-methylsulfanyl-4-oxo-5,6,7,8-tetrahydro-4H-9-thia-1,4a-diaza-fluorene-3-carboxylic acid The suspension of 4,5,6,7-tetrahydro-benzothiazol-2-yl-amine (8 gm, 0.0519 mol) and 5-(bis-ethylsulfanyl-methylene)-2,2-dimethyl-[1,3]dioxane-4,6-dione (14.2 gm, 0.0572 mol) in ethanol (60 ml) was heated at 85-90° C. for 10 hours. Reaction mixture was cooled to room temperature and filtered. The solid, thus obtained, was washed with ethanol (20 ml) followed by with diethyl ether (50 ml) and suck dried to give 7.2 gm of title compound as a solid.

¹H-NMR (400 MHz, DMSO-d₆): δ 13.55 (1H, s), 3.30-3.34 (2H, m), 2.68-2.72 (2H, m), 2.48 (3H, s), 1.88-1.92 (4H, m)

ESMS: 296.9 (M⁺+1)

Step-2: Synthesis of [(2-methylsulfanyl-4-oxo-5,6,7,8-tetrahydro-4H-9-thia-1,4a-diaza-fluorene-3-carbonyl)-amino]-acetic acid ethyl ester To the solution of acid compound as obtained in step-1 (7.0 gm, 0.0236 mol) in dichloromethane (250 ml), triethylamine (9.85 ml, 0.070 mol) and glycine ethyl ester hydrochloride (4.93 gm, 0.0354 mol) were added at room temperature. To the reaction mixture, 1-(3-dimethylaminopropyl)-3-ethylcarbodiimide hydrochloride (6.81 gm, 0.0354 mol) was added portion wise at 10-15° C. and was allowed to stir at room temperature for 14 hours. Dichloromethane was distilled off under vacuum. To the residue, water (200 ml) was added and stirred for 15 minutes. Solid, thus appeared, was filtered and washed with water. It was further slurred in mixture of ethyl acetate (20 ml) and diethyl ether (30 ml) and filtered. Solid, thus obtained, was suck dried to give 6.2 gm title compound.

¹H-NMR (400 MHz, CDCl₃): δ 9.78 (1H, bs), 4.18-4.25 (4H, m), 3.31-3.36 (2H, m), 2.64-2.69 (2H, m), 2.43 (3H, s), 1.85-1.90 (4H, m), 1.28 (3H, t)

ESMS: 382 (M⁺+1)

Step-3: Synthesis of [(2-methanesulfonyl-4-oxo-5,6,7,8-tetrahydro-4H-9-thia-1,4a-diaza-fluorene-3-carbonyl)-amino]-acetic acid ethyl ester To the cooled solution of ester compound as obtained in step-2 (6.0 gm, 0.0157 mol) in dichloromethane (60 ml), a solution of m-chloro perbenzoic acid (50-60%, 8.13 gm) in dichloromethane (80 ml) was added at 5-10° C. and stirred at same temperature for 1 hour. The reaction mixture was partitioned between dichloromethane and water. Collected organic layer was washed with sodium bicarbonate, dried over sodium sulphate and distilled off under vacuum to give crude residue which was purified by column chromatography using 1% methanol-dichloromethane. The collected fractions were evaporated to give 2.5 gm of title compound.

¹H-NMR (400 MHz, CDCl₃): δ 7.42 (1H, bs), 4.18-4.27 (4H, m), 3.36-3.37 (2H, m), 3.33 (3H, s), 2.72-2.76 (2H, m), 1.87-1.91 (4H, m), 1.30 (3H, t)

ESMS: 413.9 (M⁺+1)

Step-4: Synthesis of [(2-hydroxy-4-oxo-5,6,7,8-tetrahydro-4H-9-thia-1,4a-diaza-fluorene-3-carbonyl)-amino]acetic acid To the solution of sulfone derivative as obtained in step-3 (2.5 gm, 0.006 mol) in tetrahydrofuran, a solution of sodium hydroxide (0.75 gm, 0.0187 mol) in water (15 ml) was added and stirred at room temperature for 4 hours. Tetrahydrofuran was distilled under vacuum and the remaining solution was acidified by 1N hydrochloric acid and stirred for 30 minutes. Solid, thus appeared, was filtered and washed with ethyl acetate (25 ml) and dried under vacuum at 60° C. for 8 hours to give 1.45 gm title compound as a solid.

¹H-NMR (400 MHz, DMSO-d₆): δ 9.70 (1H, t), 4.06 (2H, d), 3.15-3.21 (2H, m), 2.60-2.70 (2H, m), 1.76-1.80 (4H, m)

ESMS: 322 (M⁺−1)

IR (KBr, CM⁻¹): 3267.9, 1734.5, 1679.9

Example-2

Preparation of [(2-hydroxy-4-oxo-6,7,8,9-tetrahydro-4H,5H-10-thia-1,4a-diaza-benzo[a]azulene-3-carbonyl)-amino]-acetic acid (Compound no. 10)

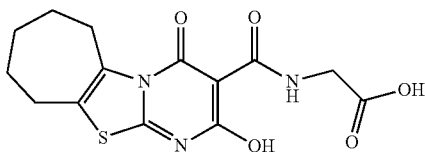 [SMILES: O=C(O)CNC(=O)c1c(O)nc2sc3c(n2c1=O)CCCCC3]

Step-1: Synthesis of 2-methylsulfanyl-4-oxo-6,7,8,9-tetrahydro-4H,5H-10-thia-1,4a-diaza-benzo[a]azulene-3-carboxylic acid The title compound was prepared from 5,6,7,8-tetrahydro-4H-cycloheptathiazol-2-yl-amine using similar method as described for step-1 of example-1.

¹H-NMR (400 MHz, DMSO-d₆): δ 3.56-3.59 (2H, m), 2.82-2.85 (2H, m), 2.42 (3H, s), 1.70-1.83 (6H, m)

ESMS: 310.9 (M⁺+1)

Step-2: Synthesis of [(2-methylsulfanyl-4-oxo-6,7,8,9-tetrahydro-4H,5H-10-thia-1,4a-diaza-benzo[a]azulene-3-carbonyl)-amino]-acetic acid ethyl ester The title compound was prepared using similar method as described for step-2 of example-1.

¹H-NMR (400 MHz, CDCl₃): δ 9.78 (1H, bs), 4.19-4.25 (4H, m), 3.66-3.69 (2H, m), 2.72-2.75 (2H, m), 2.42 (3H, s), 1.73-1.89 (6H, m), 1.27 (3H, t)

ESMS: 396 (M⁺+1)

Step-3: Synthesis of [(2-methanesulfonyl-4-oxo-6,7,8,9-tetrahydro-4H,5H-10-thia-1,4a-diaza-benzo[a]azulene-3-carbonyl)-amino]-acetic acid ethyl ester To the cooled solution of compound as obtained in step-2 (3.0 gm, 0.0076 mol) in dichloromethane (60 ml), a solution of m-chloro perbenzoic acid (50-60%, 4.50 gm) in dichloromethane (60 ml) was added at 5-10° C. and stirred at same temperature for 3 hours. Dichloromethane (100 ml) was added to reaction mixture and partitioned between dichloromethane and water. Organic layer was washed with sodium bicarbonate, dried over sodium sulphate and distilled off under vacuum to give crude residue which was stirred in diethyl ether (100 ml). The solid, thus obtained, was collected by filtration and suck dried to give 2.5 gm of title compound.

¹H-NMR (400 MHz, CDCl₃): δ 7.36 (1H, bs), 4.19-4.27 (4H, m), 3.68-3.71 (2H, m), 3.33 (3H, s), 2.80-2.83 (2H, m), 1.78-1.91 (6H, m), 1.30 (3H, t)

ESMS: 428 (M⁺+1)

Step-4: Synthesis of [(2-hydroxy-4-oxo-6,7,8,9-tetrahydro-4H,5H-10-thia-1,4a-diaza-benzo[a]azulene-3-carbonyl)-amino]-acetic acid The title compound was prepared using similar method as described for step-4 of example-1.

¹H-NMR (400 MHz, DMSO-d₆): M6.2 (1H, bs), 9.74 (1H, t), 4.06 (2H, d), 3.55-3.60 (2H, m), 2.75-2.80 (2H, m), 1.70-1.84 (6H, m)

ESMS: 335.9 (M⁺−1)

IR (KBr, CM⁻¹): 3268.2, 1739.6, 1674.6

Example-3

Preparation of 3-(carboxymethyl-carbamoyl)-2-hydroxy-4-oxo-5,8-dihydro-4H,6H-9-thia-1,4a,7-triaza-fluorene-7-carboxylicacid ethylester (Compound no. 2)

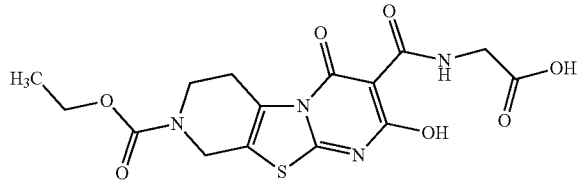 [SMILES: CCOC(=O)N1CCc2c(sc3nc(O)c(C(=O)NCC(=O)O)c(=O)n23)C1]

Step-1: Synthesis of 2-methylsulfanyl-4-oxo-5,8-dihydro-4H,6H-9-thia-1,4a,7-triaza-fluorene-3,7-dicarboxylic acid 7-ethyl ester The title compound was prepared from 2-amino-6,7-dihydro-4H-thiazolo[5,4-c]pyridine-5-carboxylic acid ethyl ester using similar method as described for step-1 of example-1

$^1$H-NMR (400 MHz, DMSO-$d_6$): δ 13.52 (1H, s), 4.60 (2H, bs), 4.09 (2H, q), 3.69 (2H, bs), 3.27 (2H, bs), 2.43 (3H, s), 1.22 ((3H, t)

ESMS: 370.1 (M$^+$+1)

Step-2: Synthesis of 3-(ethoxycarbonylmethyl-carbamoyl)-2-methylsulfanyl-4-oxo-5,8-dihydro-4H,6H-9-thia-1,4a,7-triaza-fluorene-7-carboxylic acid ethyl ester The title compound was prepared using similar method as described for step-2 of example-1.

$^1$H-NMR (400 MHz, DMSO-$d_6$): δ 9.50 (1H, t), 4.58 (2H, bs), 4.03-4.15 (6H, m), 3.67 (2H, t), 3.24-3.34 (2H, partially overlapped by water signal), 2.34 (3H, s), 1.18-1.23 (6H, m)

ESMS: 455.2 (M$^+$+1)

Step-3: Synthesis of 3-(ethoxycarbonylmethyl-carbamoyl)-2-methanesulfonyl-4-oxo-5,8-dihydro-4H,6H-9-thia-1,4a,7-triaza-fluorene-7-carboxylic acid ethyl ester The title compound was prepared using similar method as described for step-3 of example-2.

$^1$H-NMR (400 MHz, DMSO-$d_6$): δ 8.59 (1H, t), 4.62-4.68 (2H, m), 4.02-4.15 (4H, m), 3.97 (2H, d), 3.65-3.70 (2H, m), 3.34 (2H, hidden under water signal), 3.23 (3H, s), 1.18-1.28 (6H, m)

ESMS: 487.2 (M$^+$+1)

Step-4: Synthesis of 3-(carboxymethyl-carbamoyl)-2-hydroxy-4-oxo-5,8-dihydro-4H,6H-9-thia-1,4a,7-triaza-fluorene-7-carboxylic acid ethyl ester The title compound was prepared using similar method as described for step-4 of example-1.

$^1$H-NMR (400 MHz, DMSO-$d_6$): δ 16.24 (1H, s), 12.9 (1H, bs), 9.66 (1H, t), 4.55 (2H, bs), 4.07-4.11 (4H, m), 3.67 (2H, t) 3.23-3.35 (2H, partially overlapped by water signal), 1.21 (3H, t)

ESMS: 395 (M$^+$−1)

IR (KBr, CM$^{-1}$): 3260.2, 1741, 1672.8

Example-4

Preparation of {[2-hydroxy-4-oxo-7-(5-trifluoromethyl-pyridin-2-yl)-5,6,7,8-tetrahydro-4H-9-thia-1,4a,7-triaza-fluorene-3-carbonyl]-amino}-acetic acid (Compound no. 18)

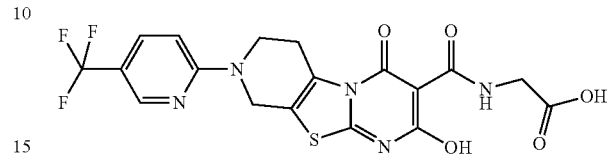

Step-1: Synthesis of (5-(5-trifluoromethyl-pyridin-2-yl)-4,5,6,7-tetrahydro-thiazolo[5,4-c]pyridin-2-ylamine)

The mixture of 1-(5-trifluoromethyl-pyridin-2-yl)-piperidine-4-one (9.9 gm, 0.0405 mol), pyrrolidine (3.53 ml, 0.0445 mol) and p-toluenesulfonic acid (100 mg) in cyclohexane (50 ml) were refluxed for 3 hours and water was removed with Dean-Stark apparatus. The resultant mixture was concentrated under reduced pressure, and the residue was dissolved in methanol (100 ml). Sulfur powder (1.05 gm, 0.0405 mol) and cynamide (1.37 gm, 0.0405 mol) were added to the solution and stirred at room temperature for overnight. The resultant solid was collected by filtration and washed with methanol (10 ml) to give 6.0 gm of title compound.

$^1$H-NMR (400 MHz, DMSO-$d_6$): δ 8.43 (1H, s), 7.82 (1H, dd), 7.04 (1H, d), 6.82 (2H, s), 4.62 (2H, s), 3.96 (2H, t), 2.55 (2H, t)

ESMS: 301 (M$^+$+1)

Step-2: Synthesis of 2-hydroxy-4-oxo-7-(5-trifluoromethyl-pyridin-2-yl)-5,6,7,8-tetrahydro-4H-9-thia-1,4a,7-triaza-fluorene-3-carboxylic acid ethyl ester The mixture of 5-(5-trifluoromethyl-pyridin-2-yl)-4,5,6,7-tetrahydro-thiazolo[5,4-c]pyridin-2-ylamine (5.7 gm, 0.019 mol) and triethyl methantricarboxylate (16.1 ml, 0.076 mol) in xylene (100 ml) was heated at 140-150° C. for 6 hours. Xylene was evaporated and diethyl ether was then added and the suspension was stirred for 15 minutes. It was filtered and washed with ether. The crude solid was digested with dichloromethane (200 ml) and filtered to remove insoluble residue. Dichloromethane layer was distilled off under vacuum to give 1.3 gm of title compound.

$^1$H-NMR (400 MHz, CDCl$_3$): δ 13.96 (1H, s), 8.44 (1H, s), 7.72 (1H, dd), 6.79 (1H, d), 4.80 (2H, s), 4.47 (2H, q), 3.94 (2H, t), 3.53-3.56 (2H, m), 1.44 (3H, t)

ESMS: 440.9 (M$^+$+1)

Step-3: Synthesis of {[2-hydroxy-4-oxo-7-(5-trifluoromethyl-pyridin-2-yl)-5,6,7,8-tetrahydro-4H-9-thia-1,4a,7-triaza-fluorene-3-carbonyl]-amino}-acetic acid ethyl ester The mixture of compound as obtained in step-2 (1.2 gm, 0.0272 mol) with glycine ethyl ester hydrochloride (0.42 gm, 0.0030 mol) was heated in dry pyridine (10 ml) at 100° C. for 5 hours. Pyridine was evaporated to dryness and residue was stirred in diethyl ether (50 ml). The solid, thus obtained, was collected by filtration and washed by ethanol (10 ml) and diethyl ether (10 ml). It was suck dried to give 260 mg of title compound.

$^1$H-NMR (400 MHz, CDCl$_3$): δ 15.99 (1H, s), 9.74 (1H, t), 8.45 (1H, s), 7.72 (1H, dd), 6.79 (1H, d), 4.80 (2H, s), 4.18-4.26 (4H, m), 3.97 (2H, t), 3.53 (2H, t), 1.30 (3H, t)

ESMS: 498 (M$^+$+1)

Step-4: Synthesis of {[2-hydroxy-4-oxo-7-(5-trifluoromethyl-pyridin-2-yl)-5,6,7,8-tetrahydro-4H-9-thia-1,4a,7-triaza-fluorene-3-carbonyl]-amino}-acetic acid The title compound was prepared using similar method as described for step-4 of example-1.

$^1$H-NMR (400 MHz, DMSO-d$_6$): δ 9.67 (1H, t), 8.48 (1H, s), 7.91 (1H, dd), 7.14 (1H, d), 4.85 (2H, s), 4.07 (2H, d), 4.01 (2H, t), 3.34 (2H, hidden under signal of water)

ESMS: 467.9 (M$^{30}$-1)

IR (KBr, CM$^{-1}$): 3292.7, 1725.7, 1677.7

Example-5

Preparation of {[7-(5-chloro-thiophene-2-sulfonyl)-2-hydroxy-4-oxo-5,6,7,8-tetrahydro-4H-9-thia-1,4a,7-triaza-fluorene-3-carbonyl]-amino}-acetic acid (Compound no. 17)

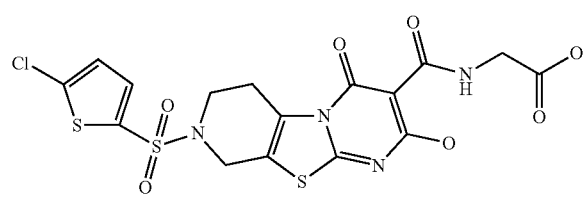 [SMILES: O=C(O)CNC(=O)c1c(O)nc2sc3c(n2c1=O)CCN(S(=O)(=O)c1ccc(Cl)s1)C3]

Step-1: Synthesis of 2-methylsulfanyl-4-oxo-5,8-dihydro-4H,6H-9-thia-1,4a,7-triaza-fluorene-3,7-dicarboxylic acid 7-tert-butyl ester The title compound was prepared from 2-amino-6,7-dihydro-4H-thiazolo[5,4-c]pyridine-5-carboxylic acid tert-butyl ester using similar method as described for step-1 of example-1.

$^1$H-NMR (400 MHz, CDCl$_3$): δ 13.38 (1H, bs), 4.56 (2H, bs), 3.76 (2H, t) 3.42 (2H, bs), 2.49 (3H, s), 1.50 (9H, s)

ESMS: 398.2 (M$^+$+1)

Step-2: Synthesis of 3-(ethoxycarbonylmethyl-carbamoyl)-2-methylsulfanyl-4-oxo-5,8-dihydro-4H,6H-9-thia-1,4a,7-triaza-fluorene-7-carboxylic acid tert-butyl ester The title compound was prepared using similar method as described for step-2 of example-1.

$^1$H-NMR (400 MHz, CDCl$_3$): δ 9.71 (1H, t), 4.52 (2H, bs), 4.18-4.25 (4H, m), 3.72 (2H, t) 3.37-3.44 (2H, m), 2.43 (3H, s), 1.50 (9H, s), 1.27 (3H, t)

ESMS: 483.2 (M$^+$+1)

Step-3: Synthesis of [(2-methylsulfanyl-4-oxo-5,6,7,8-tetrahydro-4H-9-thia-1,4a,7-triaza-fluorene-3-carbonyl)-amino]-acetic acid ethyl ester To the solution of N-Boc derivative as obtained in step-2 (19.0 gm, 0.0394 mol) in dichloromethane (60 ml), trifluoroacetic acid (60 ml) was added over 0.5 hour at 0-5° C. and stirred at room temperature for 4 hours. Solvent were distilled under vacuum and water (100 ml) was added. It was basified with sodium bicarbonate solution and resulted solid was collected by filtration. Solid was further washed by diethyl ether (50 ml) and dried under vacuum at 60° C. for 6 hours to give 11.0 gm of title compound.

$^1$H-NMR (400 MHz, CDCl$_3$): δ 9.74 (1H, bs), 4.18-4.25 (4H, m), 3.94 (2H, s), 3.34-3.37 (2H, m), 3.17 (2H, t), 2.43 (3H, s), 1.28 (3H, t)

ESMS: 382.9 (M$^+$+1)

Step-4: Synthesis of {[7-(5-chloro-thiophene-2-sulfonyl)-2-methylsulfanyl-4-oxo-5,6,7,8-tetrahydro-4H-9-thia-1,4a,7-triaza-fluorene-3-carbonyl]-amino}-acetic acid ethyl ester To the mixture of amine derivative as obtained in step-3 (1.0 gm, 0.0026 mol) and pyridine (0.31 ml, 0.0039 mol) in dichloromethane, a solution of 5-chloro-thiophene-2-sulfonyl chloride (0.62 gm, 0.00287 mol) in dichloromethane (5 ml) was added at 0-5° C. and stirred at room temperature for 4 hours. Reaction mixture was poured into water (50 ml) and extracted with dichloromethane (50 ml×2). The combined organic layer was dried over sodium sulphate and distilled off under vacuum to yield a solid, which was slurred in ethylactate (10 ml). It was filtered and suck dried to give 980 mg of title compound.

$^1$H-NMR (400 MHz, DMSO-d$_6$): δ 9.42-9.48 (1H, m), 7.68 (1H, d), 7.39 (1H, d), 4.32-4.36 (2H, m), 4.02-4.13 (4H, m), 3.38-3.51 (4H, hidden under signal of water), 2.34-2.36 (3H, m), 1.15-1.22 (3H, m)

ESMS: 564.8 (M$^+$+1)

Step-5: {[7-(5-Chloro-thiophene-2-sulfonyl)-2-methanesulfonyl-4-oxo-5,6,7,8-tetrahydro-4H-thia-1,4a,7-triaza-fluorene-3-carbonyl]-amino}-acetic acid ethyl ester To the cooled solution of compound as obtained in step-4 (950 mg, 0.0017 mol) in dichloromethane (20 ml), a solution of m-chloro perbenzoic acid (50-60%, 0.72 gm) in dichloromethane (30 ml) was added at 5-10° C. and stirred at room temperature for 2 hours. Reaction mixture was poured into water (100 ml) and extracted with dichloromethane (50 ml×2). Organic layer was washed with sodium bicarbonate, dried over sodium sulphate and distilled off under vacuum to give 800 mg as a crude solid, which was used for next step without purification.

Step-6: Synthesis of {[7-(5-chloro-thiophene-2-sulfonyl)-2-hydroxy-4-oxo-5,6,7,8-tetrahydro-4H-9-thia-1,4a,7-triaza-fluorene-3-carbonyl]-amino}-acetic acid A mixture of compound as obtained in step 5 (0.8 g, 0.0013 mol) in tetrahydrofuran (20 ml), a solution of sodium hydroxide (160 mg, 0.004 mol) in water (20 ml) was added. The reaction mixture was stirred at room temperature for 2 hours. Solvent was distilled off under vacuum and remaining mass was acidified with dilute hydrochloric acid and precipitate was appeared, which was collected by filtration and washed with diethyl ether (40 ml). Solid was dried under vacuum to give 220 mg of title compound.

$^1$H-NMR (400 MHz, DMSO-$d_6$): δ 16.28 (1H, s), 12.9 (1H, bs), 9.64 (1H, t), 7.65 (1H, d), 7.39 (1H, d), 4.30-4.40 (2H, m), 4.08 (2H, d), 3.40-3.50 (2H, m), 3.34 (2H, hidden under signal of water)

ESMS: 502.9 (M$^+$−1)

IR (KBr, CM$^{-1}$): 3304.8, 1714.3, 1682.3

Example-6

Preparation of 2-Methylsulfanyl-4-oxo-6,7,8,9-tetrahydro-4H,5H-10-thia-1,4a-diaza-benzo[a]azulene-3-carboxylic acid (2-oxo-2-pyrrolidin-1-yl-ethyl)-amide (Compound no. 79)

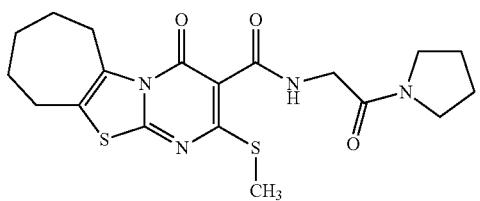 [SMILES: CSc1nc2sc3c(n2c(=O)c1C(=O)NCC(=O)N1CCCC1)CCCCC3]

Step-1: Synthesis of [(2-Methylsulfanyl-4-oxo-6,7,8,9-tetrahydro-4H,5H-10-thia-1,4a-diaza-benzo[a]azulene-3-carbonyl)-amino]-acetic acid The title compound was prepared using similar hydrolysis conditions as described for step-4 of example-1 starting from [(2-methylsulfanyl-4-oxo-6,7,8,9-tetrahydro-4H,5H-10-thia-1,4a-diaza-benzo[a]azulene-3-carbonyl)-amino]-acetic acid ethyl ester (step-2 of example-2).

$^1$H-NMR (400 MHz, DMSO-$d_6$): δ 9.50 (1H, t), 3.97 (2H, d), 3.58-3.61 (2H, m), 2.79-2.81 (2H, m), 2.32 (3H, s), 1.81-1.82 (2H, m), 1.70-1.71 (4H, m)

ESMS: 368.1 (M$^+$+1)

Step-2: Synthesis of 2-Methylsulfanyl-4-oxo-6,7,8,9-tetrahydro-4H,5H-10-thia-1,4a-diaza-benzo[a]azulene-3-carboxylic acid (2-oxo-2-pyrrolidin-1-yl-ethyl)-amide To the stirred solution of compound obtained in step-1 (1.0 gm, 0.0027 mole) in dichloromethane (20 ml), triethylamine (1.13 ml, 0.0082 mole) and pyrrolidine (0.29 gm, 0.0040 mole) were added. To the reaction mixture, 1-(3-dimethylaminopropyl)-3-ethylcarbodiimide hydrochloride (0.78 gm, 0.0040 mole) was added and stirred at room temperature for 12 hrs. Organic layer was washed with 1N hydrochloric acid (50 ml) and sodium bicarbonate solution. Organic solvent was distilled off to yield a solid, which was stirred in methanol (20 ml), filtered and suck dried to give 0.35 gm of title compound.

$^1$H-NMR (400 MHz, CDCl$_3$): δ 10.07 (1H, bs), 4.18 (2H, d), 3.69-3.71 (2H, m), 3.53 (2H, t), 3.42 (2H, t), 2.70-2.73 (2H, m), 2.41 (3H, s), 1.96-2.04 (2H, m), 1.75-1.90 (8H, m)

ESMS: 421.1 (M$^+$+1)

IR (KBr, CM$^{-1}$): 3297.3, 1650.9, 1601.8

Example-7

Preparation of [(2-Ethoxy-4-oxo-6,7,8,9-tetrahydro-4H,5H-10-thia-1,4a-diaza-benzo[a]azulene-3-carbonyl)-amino]-acetic acid (Compound no. 81)

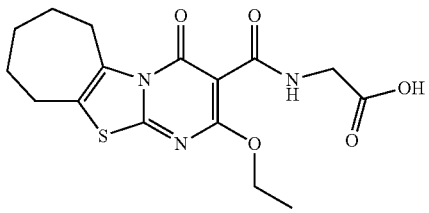 [SMILES: CCOc1nc2sc3c(n2c(=O)c1C(=O)NCC(=O)O)CCCCC3]

Step-1: Synthesis of [(2-Ethoxy-4-oxo-6,7,8,9-tetrahydro-4H,5H-10-thia-1,4a-diaza-benzo[a]azulene-3-carbonyl)-amino]-acetic acid ethyl ester The mixture of compound obtained in step-3 of example-2 (1.00 gm, 0.0023 mole) and sodium ethoxide (0.318 gm, 0.0046 mole) in ethanol (20 ml) was stirred at 80° C. for 15 min and then 10 hr at room temperature. The reaction mixture was poured into 1N HCl and extracted with ethyl acetate (50 ml×2). Ethyl acetate was distilled off and crude residue was purified using 20% ethyl acetate in hexane. The fractions were distilled off to give 150 mg of title compound.

$^1$H-NMR (400 MHz, CDCl$_3$): δ 9.20 (1H, t), 4.49 (2H, q), 4.18-4.24 (4H, m), 3.65-3.68 (2H, m), 2.70-2.73 (2H, m), 1.78-1.88 (6H, m), 1.43 (3H, t), 1.26 (3H, t)

ESMS: 394.1 (M$^+$+1)

Step-2: Synthesis of [(2-Ethoxy-4-oxo-6,7,8,9-tetrahydro-4H,5H-10-thia-1,4a-diaza-benzo[a]azulene-3-carbonyl)-amino]-acetic acid The title compound was prepared using similar hydrolytic condition as described for step-4 of example-1.

$^1$H-NMR (400 MHz, DMSO-$d_6$): δ 12.50 (1H, bs), 8.61 (1H, t), 4.34 (2H, q), 3.88 (2H, d), 3.59-3.61 (2H, m), 2.76-2.79 (2H, m), 1.68-1.81 (6H, m), 1.27 (3H, t)

ESMS: 364.3 (M$^+$−1)

IR (KBr, CM$^{-1}$): 3316.2, 1711.9, 1655.8

Example-8

Preparation of 2-Hydroxy-4-oxo-6,7,8,9-tetrahydro-4H,5H-10-thia-1,4a-diaza-benzo[a]azulene-3-carboxylic acid cyclohexylcarbamoylmethyl-amide (Compound No. 98)

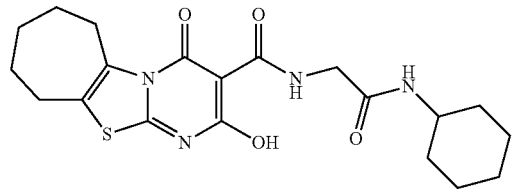 [SMILES: O=C(CNC(=O)c1c(O)nc2sc3c(n2c1=O)CCCCC3)NC1CCCCC1]

To the stirred suspension of [(2-hydroxy-4-oxo-6,7,8,9-tetrahydro-4H,5H-10-thia-1,4a-diaza-benzo[a]azulene-3-carbonyl)-amino]-acetic acid (0.70 gm, 0.0020 mole) in dichloromethane (20 ml), triethylamine (0.85 ml, 0.0062 mole) and cyclohexylamine (0.29 ml, 0.0025 mole) were added. To the reaction mixture, hydroxybenzotriazole (0.28 gm, 0.0020 mole) and 1-(3-dimethylaminopropyl)-3-ethyl-carbodiimide hydrochloride (0.60 gm, 0.0031 mole) were added and stirred at room temperature for 12 hrs. Dichloromethane was distilled off and 1N hydrochloric acid (50 ml) was added to the residue, the separated solid was collected by filtration. The solid thus obtained was stirred in methanol (20 ml) at 60° C. for 0.5 hr, filtered and suck dried to give 0.60 gm title compound.

$^1$H-NMR (400 MHz, CDCl$_3$): δ 15.74 (1H, s), 9.94 (1H, t), 5.86 (1H, d), 4.05 (2H, d), 3.75-3.82 (1H, m), 3.63-3.65 (2H, m), 2.69-2.72 (2H, m), 1.78-1.93 (8H, m), 1.66-1.71 (2H, m), 1.58-1.61 (2H, m), 1.34-1.37 (2H, m), 1.14-1.16 (2H, m).

ESMS: 417.2 (M$^+$−1)

IR (KBr, CM$^{-1}$): 2929.3, 1671.4, 1653.4

The following representative compounds of the present invention were prepared in analogus manner by using the synthetic schemes as described above:

TABLE 1

| Comp. No. | $^1$H-NMR (400 MHz, DMSO-d$_6$) | MASS | IR (KBr, CM$^{-1}$) |
|---|---|---|---|
| 3 | δ 16.27 (1H, s), 12.9 (1H, bs), 9.67(1H, t), 4.38-4.43(2H, m), 4..08 (2H, d), 3.52(2H, bs), 3.34(2H, hidden under signal of water) 3.01(3H, s) | 403.1 (M$^+$ + 1) | IR (KBr, CM$^{-1}$): 3263.9, 1746.3 , 1625.3 |
| 4 | δ 16.26 (1H, s), 12.9 (1H, bs), 9.67(1H, t), 4..61-4.68(2H, m), 4.07-4..08(2H, m), 3..76 (2H, t), 3.28-3.34(2H, partailly overlapped by water signal) 2.25-2.33(2H, m), 1.98-2.04(1H, m), 0.90-0.93 (6H, m) | 409.1 (M$^+$ + 1) | IR (KBr, CM$^{-1}$): 3289.2, 1731.6, 1677.1 |
| 5 | δ 16.26 (1H, s), 12.9 (1H, bs), 9.67(1H, t), 4..46-4.50(2H, m), 4.08(2H, d), 3.61 (2H, t), 3.34-3.50 (3H, partailly overlapped by water signal), 1.25(6H, d) | 431.1 (M$^+$ + 1) | IR (KBr, CM$^{-1}$): 3302.8, 1717.7, 1682.6 |
| 6 | δ 15.98(1H, s), 12.7(1H, bs), 9.81(1H, s), 3.15-3.25(2H, m), 2.60-2.68 (2H, m), 2.15-2.25(2H, m), 1.90-2.00(2H, m), 1.68-1.80(8H, m) | 376.1 (M$^+$ − 1) | IR (KBr, CM$^{-1}$): 3228.9, 1732.3, 1631.2 |
| 7 | δ 12.9 (1H, bs), 9.62(1H, t), 7.71(2H, d), 7.45 (2H, d), 4..24 (2H, s), 4.07(2H, d), 3.24-3.33 (4H, partially overlapped by water signal), 2.38 (3H, s) | 479.1 (M$^+$ + 1) | IR (KBr, CM$^{-1}$): 3307.2, 1716.9, 1640.8 |
| 8 | δ 12.9 (1H, bs), 9.68 (1H, t), 8.79 (1H, s), 7.45-7.47 (2H, m), 7.25 (2H, t), 6.96 (1H, t), 4..61-4.91 (2H, m), 4.09 (2H, d), 3.79 (2H, bs), 3.30-3.40 (2H, hidden under signal of water) | 441.9 (M$^+$ − 1) | IR (KBr, CM$^{-1}$): 3273.8, 1736.9, 1680.9 |
| 9 | δ 16.22 (1H, s), 9.67(1H, t), 4..61-4.91(2H, m), 3.77-4.09 (4H, m), 3.34 (2H, hidden under signal of water), 1.95-2.14 (1H, m), 0.79 (4H, m) | 390.9 (M$^+$ − 1) | IR (KBr, CM$^{-1}$): 3280.4, 1728.0, 1673.7 |
| 11 | δ 16.11 (1H, bs), 9.69 (1H, t), 4.08 (2H, d), 3.21(2H, t), 2.84 (2H, t), 2.38-2.42 (2H, m) | 308.0 (M$^+$ − 1) | IR (KBr, CM$^{-1}$): 3241.2, 1731.0, 1674.5 |
| 12 | δ 9.97(1H, t), 3.44 (2H, d), 3.04-3.12 (2H, m), 2.46 (2H, partially overlapped by solvent signal), 1.65-1.80(4H, m), | 322.2 (M$^+$ − 1) | IR (KBr, CM$^{-1}$): 2941.5, 1648.1, 1555.9 |
| 13 | δ 9.70(1H, t), 4..07 (2H, d), 3.47-3.51 (1H, m), 2.80-3.00 (1H, m), 2.62-2.78 (1H, m), 2.35-2.42 (1H, m), 1.95-2.10(1H, m), 1.40-1.55(1H, m), 1.25-1.35(1H, m), 0.92 (9H, s) | 378 (M$^+$ − 1) | IR (KBr, CM$^{-1}$): 3277.9, 1739.8, 1684.3 |
| 14 | δ 16.43 (1H, s), 12.39 (1H, s), 9.58 (1H, t), 3.54 (2H, q), 3.19 (2H, t), 2.82 (2H, t), 2.50-2.55 (2H, partailly overlapped by solvent signal), 2.35-2.45(2H, m) | 321.9 (M$^+$ − 1) | IR (KBr, CM$^{-1}$): 3292.5, 1722.0, 1680.3 |
| 15 | $^1$H-NMR (400 MHz, CDCl$_3$) δ 16.21 (1H, s), 9.67(1H, s), 3.68-3.72 (2H, m), 3.55-3.60 (1H, m), 2.90-3.10(1H, m), 2.60-2.74 (3H, m), 2.35-2.45 (1H, m), 2.05-2.15(1H, m), 1.45-1.60(1H, m), 1.30-1.40 (1H, m) 0.95 (9H, s) | 394.1 (M$^+$ + 1) | IR (KBr, CM$^{-1}$): 3289.6, 1721.8, 1635.6 |
| 16 | δ 16.24 (1H, bs), 9.67 (1H, t), 7.55-7.58 (2H, m), 7.32 (2H, t), 4.60-4.80 (2H, m), 4..09 (2H, d), 3.80-3.90(1H, bs), 3.55-3.65(1H, m), 3.35 (2H, hidden under signal of water) | 444.9 (M$^+$ − 1) | IR (KBr, CM$^{-1}$): 3257.1, 1725.7, 1668.1 |
| 19 | δ 9.63 (1H, t), 7.98 (2H, d), 7.62 (2H, d), 4.30 (2H, bs), 3.98 (2H, d), 3.47-3.50 (2H, m, partially overlapped by water signal), 3.23-3.33 (2H, hidden under signal of water) | 546.9 (M$^+$ − 1) | IR (KBr, CM$^{-1}$): 3289.5, 1739.7, 1673.8 |
| 20 | δ 9.67 (1H, t), 4.68 (2H, bs), 4.08 (2H, d), 3.85 (2H, t), 3.34 (2H, hidden under signal of water), 1.23 (9H, s) | 407 (M$^+$ − 1) | IR (KBr, CM$^{-1}$): 3275.9, 1740.4, 1673.8 |
| 21 | δ 16.24 (1H, s), 9.68 (1H, t), 7.40 (2H, d), 7.31 (2H, d), 4.60-4.80 (2H, bs), 4.09 (2H, d), 3.50-3.80 (2H, m), 3.37 (2H, hidden under signal of water), 2.63 (2H, t) 1.58 (2H, m), 1.32-1.40 (2H, m), 0.91(3H, t) | 483.1 (M$^+$ − 1) | IR (KBr, CM$^{-1}$): 3268.1, 1729.5, 1683.3 |
| 22 | δ 9.69 (1H, t), 7.64 (2H, d), 7.48 (2H, d), 4.58-4.75(2H, m), 3.76-4.03 (4H, m), 3.35-3.65 (2H, partially overlapped by water signal)) | 511 (M$^+$ − 1) | IR (KBr, CM$^{-1}$): 3272.1, 1725.4, 1683.7 |
| 23 | δ 16.19(1H, bs), 9.68 (1H, t), 7.37-7.42 (4H, m), 4.07 (2H, d), 3.70 (2H, s), 3.46-3.54 (2H, m), 3.20-3.33 (2H, partially overlapped by water signal), 2.80 (2H, t) | 447 (M$^+$ − 1) | IR (KBr, CM$^{-1}$): 3263.7, 1732.1, 1682.7 |

TABLE 1-continued

| Comp. No. | $^1$H-NMR (400 MHz, DMSO-$d_6$) | MASS | IR (KBr, CM$^{-1}$) |
|---|---|---|---|
| 24 | δ 9.63-9.69 (2H, m), 7.30-7.34 (2H, m), 7.16 (2H, t), 5.10 (2H, bs), 4.16 (2H, t), 4.06 (2H, d), 3.34-3.50 (2H, partailly overlapped by water signal) | 476 (M$^+$ − 1) | IR (KBr, CM$^{-1}$): 3267.2, 1720.3, 1681.8 |
| 25 | δ 16.2 (1H, bs) 9.67 (1H, t), 7.63 (1H, d), 5.00 (2H, s), 4.52-4.54 (1H, m), 4.02-4.10 (4H, m), 3.34 (2H, hidden under signal of water), 1.17(6H, d) | 424 (M$^+$ − 1) | IR (KBr, CM$^{-1}$): 3266.4, 1718.4, 1681.3 |
| 26 | δ 16.26 (1H, bs), 9.67 (1H, t), 7.33-7.40 (5H, m), 5.15 (2H, s), 4.59 (2H, bs), 4.07 (2H, d), 3.72 (2H, bs), 3.33 (2H, hidden under signal of water) | 457 (M$^+$ − 1) | IR (KBr, CM$^{-1}$): 3282.0, 1676.2, 1564.9 |
| 27 | δ 16.2 (1H, bs) 9.67 (1H, t), 4.61-4.64 (2H, m), 4.08 (2H, d), 3.72-3.76 (2H, m), 3.20-3.31 (2H, partailly overlapped by water signal), 2.32-2.40 (2H, m), 0.98-1.08 (1H, m), 0.45-0.47 (2H, m), 0.13-0.15 (2H, m), | 405.1 (M$^+$ − 1) | IR (KBr, CM$^{-1}$): 3300.5, 1728.2, 1677.8 |
| 28 | δ 9.66(1H, t), 7.24-7.39 (4H, m), 4.62-4.72 (2H, m), 4.08 (2H, d), 3.75-3.86 (4H, m), 3.20-3.30 (2H, m), | 475.1 (M$^+$ − 1) | IR (KBr, CM$^{-1}$): 3287.9, 1731.1, 1675.3 |
| 29 | δ 16.21 (1H, bs), 12.9 (1H, bs), 9.67 (1H, t), 4.60-4.67 (2H, m), 4.08-4.09 (2H, m), 3.75 (2H, t), 3.15-3.3 l(2H, partailly overlapped by water signal), 2.39-2.47 (2H, m, partailly overlapped by solvent signal), 2.14-2.16(1H, m), 1.73-1.77 (2H, m), 1.40-1.60(4H, m), 1.00-1.20 (2H, m) | 433.0 (M$^+$ − 1) | IR (KBr, CM$^{-1}$): 3304.6, 1731.2, 1675.7 |
| 30 | δ 12.5 (1H, bs), 9.66 (1H, t), 3..51-3.54 (4H, m), 2.72-2.80 (2H, m), 2.50-2.55 (2H, partailly overlapped by solvent signal), 1.60-1.85(6H, m) | 352 (M$^+$ + 1) | IR (KBr, CM$^{-1}$): 3198.0, 1731.9, 1670.1 |
| 31 | δ 9.69 (1H, bs), 7.27 (2H, d), 6.91 (2H, d), 4.06 (2H, d), 3.75 (3H, s), 3.64 (2H, bs), 3.49 (2H, bs), 3.24 (2H, partailly overlapped by water signal), 2.78 (2H, bs) | 443.2 (M$^+$ − 1) | IR (KBr, CM$^{-1}$): 3259.2, 1678.9, 1611.6 |
| 32 | δ 16.09 (1H, bs), 13.1 (1H, bs), 9.87 (1H, d), 4.46-4.49 (1H, m), 3.55-3.65 (2H, m), 2.70-2.80 (2H, m), 1.77-1.85 (2H, m), 1.65-1.75(4H, m), 1.42 (3H, d) | 349.8 (M$^+$ − 1) | IR (KBr, CM$^{-1}$): 3261.1, 1736.2, 1684.0 |
| 33 | δ 9.69 (1H, t), 8.56 (1H, s), 7.99(1H, bs) 7.66 (1H, d), 4.62-4.76(2H, m), 4.03 (2H, d), 3.80-3.95 (2H, m) 3.36-3.65 (2H, partailly overlapped by water signal), | 461.9 (M$^+$ − 1) | IR (KBr, CM$^{-1}$): 3262.6, 1634.1, 1538.8 |
| 34 | δ 16.17 (1H, s), 9.72 (1H, t), 4.08 (2H, t), 3.19 (2H, t), 2.44 (2H, s), 1.57 (2H, t), 1.00 (6H, s) | 349.9 (M$^+$ − 1) | IR (KBr, CM$^{-1}$): 3256.9, 1718.7, 1680.8 |
| 35 | δ 16.24 (1H, bs), 9.67 (1H, t), 7.65 (1H, d), 7.57 (1H, d), 4.83 (2H, bs), 4.08 (2H, d), 3.96 (2H, t), 3.34 (2H, hidden under signal of water) | 434.9 (M$^+$ − 1) | IR (KBr, CM$^{-1}$): 3300.7, 1716.5, 1679.7 |
| 36 | δ 16.26 (1H, bs), 9.69 (1H, t), 8.45 (1H, dd), 8.17 (1H, dd), 7.02 (1H, dd), 4.72 (2H, s), 4.07 (2H, d), 3.94 (2H, t), 3.35-3.46 (2H, partailly overlapped by water signal) | 426.8 (M$^+$ + 1) | IR (KBr, CM$^{-1}$): 3375.9, 1718.6, 1675.7 |
| 37 | δ 16.25 (1H, s), 9.67(1H, t), 7.56 (1H, d), 7.46 (1H, dd), 7.24 (1H, d), 4.68 (2H, bs), 4.09 (2H, d), 3.91(3H, s), 3.34 (4H, hidden under signal of water) | 490.8 (M$^+$ − 1) | IR (KBr, CM$^{-1}$): 3376.0, 1702.0, 1647.0 |
| 38 | δ 16.20 (1H, s), 9.76(1H, t), 4.08 (2H, d), 3.34 (2H, hidden under signal of water), 2.80-2.82 (2H, m), 1.72.1.74 (2H, m), 1.61-1.63 (2H, m), 1.49-1.51 (2H, m), 1.32-1.35 (2H, m) | 350.0 (M$^+$ − 1) | IR (KBr, CM$^{-1}$): 3267.8, 1736.2, 1677.8 |
| 39 | $^1$H-NMR (400 MHz, CDCl$_3$): δ 16.04 (1H, bs), 9.74 (1H, bs), 7.08-7.26 (3H, m), 4.16-4.18 (2H, m), 3.73-3.75 (2H, m), 3.52-3.54 (2H, m), 3.39-3.41 (2H, m), 2.88-2.92 (6H, m), 2.06-2.10 (2H, m) | 453.1 (M$^+$ − 1) | IR (KBr, CM$^{-1}$): 3295.0, 1674.8, 1633.3 |
| 40 | δ 16.05 (1H, s), 9.86 (1H, d), 4.47-4.49 (1H, m), 3.19 (2H, t), 2.44 (2H, s), 1.56 (2H, t), 1.42 (3H, d), 1.00 (6H, s) | 364.2 (M$^+$ − 1) | IR (KBr, CM$^{-1}$): 3254.2, 1738.1, 1533.3 |
| 41 | δ 9.67 (1H, bs), 6.59-6.61 (3H, m), 4.58-4.73 (2H, m), 4.06 (2H, d), 3.87-3.88 (m, 2H), 3.77 (6H, s), 3.36-3.65 (2H, partailly overlapped by water signal), | 480.0 (M$^+$ + 1) | IR (KBr, CM$^{-1}$): 3065.4, 1725.1, 1629.6 |
| 42 | δ 16.25 (1H, s), 9.67 (1H, t), 8.02 (2H, d), 7.75 (2H, d), 4.79 (1.2H, bs), 4.54 (0.8H, bs), 4.09 (2H, d), 3.95 (0.8H, bs), 3.57 (1.2H, bs), 3.34 (2H, hidden under signal of water), 3.28 (3H, s), | 505.0 (M$^+$ − 1) | IR (KBr, CM$^{-1}$): 3284.4, 1742.8, 1685.0 |
| 43 | δ 16.00 (1H, s), 9.89 (1H, d), 4.44-4.45 (1H, m), 3.20 (2H, t), 2.44 (2H, s), 2.19-2.23(1H, m), 1.56 (2H, t), 1.00 (6H, s), 0.92-0.95 (6H, m) | 392.2 (M$^+$ − 1) | IR (KBr, CM$^{-1}$): 3261.2, 1736.1, 1682.0 |
| 44 | δ 16.04 (1H, s), 9.85 (1H, d), 4.47-4.50 (1H, m), 3.19 (2H, t), 2.44 (2H, s), 1.56 (2H, t), 1.42 (3H, d), 1.00 (6H, s) | 366.0 (M$^+$ + 1) | IR (KBr, CM$^{-1}$): 3265.3, 1738.3, 1689.8 |
| 45 | δ 9.70 (1H, bs), 7.63(2H, s), 4.60-4.72 (2H, m), 4.01 (2H, d), 3.77-3.88 (5H, m) 3.35-3.60 (2H, partailly overlapped by water signal) | 526.9 (M$^+$ − 1) | IR (KBr, CM$^{-1}$): 3255.7, 1741.6, 1673.2 |
| 46 | δ 9.74 (1H, bs), 8.04-8.07(3H, m), 3.91-3.93 (4H, m), 3.59-3.61 (2H, m) 3.35 (2H, merged with water signal), 2.86 (2H, t) | 549.2 (M$^+$ − 1) | IR (KBr, CM$^{-1}$): 3267.6, 1731.4, 1679.5 |

TABLE 1-continued

| Comp. No. | $^1$H-NMR (400 MHz, DMSO-$d_6$) | MASS | IR (KBr, CM$^{-1}$) |
|---|---|---|---|
| 47 | δ 9.67 (1H, bs), 7.40 (2H, d), 7.30 (2H, d), 4.70 (2H, bs), 4.08 (2H, d), 3.62-3.90 (2H, m), 3.34 (2H, merged with water signal), 2.61 (2H, t), 1.57-1.66 (2H, m), 0.91 (3H, t) | 469.1 (M$^+$ − 1) | IR (KBr, CM$^{-1}$): 3270.1, 1742.6, 1683.5 |
| 48 | δ 9.67 (1H, t), 8.22-8.28 (3H, m), 4.79 (1H, bs), 4.57 (1H, bs), 4.07 (2H, d), 3.95 (1H, bs), 3.57-3.36 (3H, partailly overlapped by water signal) | 563.1 (M$^+$ − 1) | IR (KBr, CM$^{-1}$): 3269.7, 1722.9, 1691.7 |
| 49 | δ 9.69 (1H, t), 7.61-7.63 (2H, m), 7.37 (1H, dd), 4.05 (2H, d), 3.72 (2H, s), 3.54 (2H, bs) 3.26 (2H, partailly overlapped by water signal), 2.82 (2H, t) | 481.1 (M$^+$ − 1) | IR (KBr, CM$^{-1}$): 3247.9, 1733.0, 1684.3 |
| 52 | δ 9.79 (1H, bs), 7.72 (2H, d), 7.59 (2H, d), 3.81 (2H, bs), 3.76 (2H, d), 3.38-3.52 (2H, partailly overlapped by water signal), 3.26-3.38 (2H, partailly overlapped by water signal), 2.83(2H, t) | 482.9 (M$^+$ + 1) | IR (KBr, CM$^{-1}$): 3279.6, 1734.1, 1681.1 |
| 53 | δ 16.13 (1H, s), 9.71 (1H, t), 4.08 (2H, d), 3.14 (2H, t), 2.43 (2H, s), 1.59 (2H, t), 1.30-1.37 (4H, m), 0.80 (6H, t) | 380.0 (M$^+$ + 1) | IR (KBr, CM$^{-1}$): 3227.6, 1741.8, 1676.6 |
| 54 | δ 16.05 (1H, s), 9.95 (1H, s), 3.18 (2H, t), 2.44 (2H, s), 1.53-1.56 (8H, m), 1.00 (6H, s) | 378.2 (M$^+$ − 1) | IR (KBr, CM$^{-1}$): 3228.7, 1730.4, 1688.6 |
| 55 | δ 15.81(1H, bs), 10.38 (1H, d), 7.32-7.41 (5H, m), 5.50 (1H, d), 3.20 (2H, t), 2.44 (2H, s), 1.56 (2H, t), 1.0 (6H, s) | 428.0 (M$^+$ + 1) | IR (KBr, CM$^{-1}$): 29.8.0, 1732.1, 1683.7 |
| 56 | δ 16.22(1H, s), 9.72 (1H, t), 8.50 (1H, d), 7.84-7.85 (2H, m), 7.47-7.54 (3H, m), 4.25-4.35 (1H, m), 4.09 (2H, d), 3.35-3.50 (1H, partially overlapped by water signal), 3.10-3.35 (1H, partially overlapped by water signal), 2.95-3.05 (1H, m), 2.60-2.70 (1H, m), 2.00-2.10 (1H, m), 1.85-1.95 (1H, m) | 441.1 (M$^+$ − 1) | IR (KBr, CM$^{-1}$): 3323.0, 1733.9, 1670.7 |
| 57 | δ 16.39(1H, s), 9.64 (1H, t), 4.08(2H, d), 2.93-2.94 (2H, m), 2.60-2.62 (2H, m), 1.78-1.82 (4H, m), | 306.3 (M$^+$ − 1) | IR (KBr, CM$^{-1}$): 3251.2, 1736.7, 1676.9 |
| 58 | δ 16.18 (1H, s), 9.71 (1H, t), 4.08 (2H, d), 3.34 (1H, merged with water signal), 2.90-3.10 (1H, m), 2.72-2.80 (1H, m), 2.20-2.30 (1H, m), 1.85-1.95 (2H, m), 1.40-1.50 (1H, m), 1.04 (3H, d), | 336.1 (M$^+$ − 1) | IR (KBr, CM$^{-1}$): 3256.9, 1733.5, 1674.4 |
| 59 | δ 16.16 (1H, s), 9.70 (1H, t), 4.08 (2H, d), 3.34-3.40 (1H, partially overlapped by water signal), 2.90-3.10 (1H, m), 2.70-2.80 (1H, m), 2.20-2.30 (1H, m), 1.85-1.95 (1H, m), 1.60-1.70 (1H, m), 1.30-1.40 (5H, m), 0.90 (3H, t) | 364.1 (M$^+$ − 1) | IR (KBr, CM$^{-1}$): 3278.8, 1732.3, 1674.7 |
| 60 | δ 16.16(1H, s), 9.72 (1H, t), 4.07 (2H, d), 3.01 (2H, s), 2.65 (2H, t), 1.56 (2H, t), 1.00 (6H, s) | 350.1 (M$^+$ − 1) | IR (KBr, CM$^{-1}$): 3267.9, 1745.4, 1682.4 |
| 61 | $^1$H-NMR (400 MHz, CDCl$_3$): δ 4.15 (2H, s), 3.27 (2H, t), 3.14 (3H, s), 2.41 (2H, s), 1.62 (2H, t), 1.06 (6H, s) | 364.1 (M$^+$ − 1) | IR (KBr, CM$^{-1}$): 2937.1, 1722.9, 1689.4 |
| 62 | $^1$H-NMR (400 MHz, CDCl$_3$ + CD$_3$OD): δ 15.61(1H, s), 9.87 (1H, s), 3.30 (2H, merged with solvent peak), 2.41 (2H, s), 2.22-2.25 (2H, m), 1.88-1.95 (2H, m), 1.42-1.74 (6H, m), 1.22-1.37 (2H, m), 1.06 (6H, s) | 418.1 (M$^+$ − 1) | IR (KBr, CM$^{-1}$): 2951.5, 1733.3, 1672.8 |
| 63 | $^1$H-NMR (400 MHz, CDCl$_3$): δ 4.44-4.60 (1H, m), 3.68-3.70 (1H, m), 3.15-3.31 (4H, m), 2.58-2.63 (1H, m), 2.51 (3H, s), 2.41 (2H, s), 1.77-2.05 (4H, m), 1.60 (2H, t), 1.05 (6H, s) | 434.1 (M$^+$ − 1) | IR (KBr, CM$^{-1}$): 2953.3, 1727.7, 1670.7 |
| 64 | δ 9.71 (1H, t), 7.24-7.35 (5H, m), 4.08 (2H, d), 2.94-3.05 (3H, m), 2.78-2.81 (2H, m), 1.97-2.07 (2H, m), | 398.1 (M$^+$ − 1) | IR (KBr, CM$^{-1}$): 2925.5, 1738.2, 1675.1 |
| 65 | δ 16.22 (1H, s), 9.67(1H, t), 4.65 (2H, s), 4.08 (2H, d), 3.91 (2H, t), 3.25 (2H, m) | 324.1 (M$^+$ − 1) | IR (KBr, CM$^{-1}$): 3294.2, 1731.9, 1669.6 |
| 66 | δ 16.20 (1H, s), 9.72(1H, t), 4.07 (2H, d), 3.20-3.24 (1H, m), 2.77-2.82 (2H, m), 1.68-1.70(1H, m), 1.22-1.27 (4H, m), 1.08 (3H, s), 0.93 (3H, s) | 364.1 (M$^+$ − 1) | IR (KBr, CM$^{-1}$): 3272.8, 1743.6, 1682.4 |
| 67 | δ 9.64 (1H, t), 4.60(2H, s), 4.09 (2H, d), 3.79 (2H, t), 2.30-2.32 (2H, m) | 372.0 (M$^+$ − 1) | IR (KBr, CM$^{-1}$): 3277.2, 1741.5, 1672.5 |
| 68 | δ 12.67 (1H, bs), 9.47 (1H, t), 3.97 (2H, d), 3.84 (2H, s), 3.49 (2H, t), 2.96 (2H, t), 2.34 (3H, s) | 372.0 (M$^+$ + 1) | IR (KBr, CM$^{-1}$): 3260.4, 1731.0, 1659.6 |
| 69 | $^1$H-NMR (400 MHz, CDCl$_3$): δ 9.85 (1H, t), 5.40 (1H, s), 4.13-4.30 (4H, m), 3.83-3.87 (1H, m), 3.65-3.69 (1H, m), 2.72-2.74 (1H, m) 2.62-2.66 (1H, m), 2.42 (3H, s), 2.24-2.28 (1H, m), 2.07-2.09 (1H, m), 1.87-1.89 (1H, m), 1.63-1.68 (1H, m), 1.29 (3H, t), 1.21 (3H, t) | 426.0 (M$^+$ + 1) | IR (KBr, CM$^{-1}$): 3247.9, 1748.2, 1667.6 |
| 70 | δ 16.18 (1H, s), 9.71 (1H, t), 4.08 (2H, d), 3.25 (2H, t), 2.54 (2H, s), 1.60 (2H, t), 0.45-0.47 (4H, m) | 348.1 (M$^+$ − 1) | IR (KBr, CM$^{-1}$): 3266.4, 1716.9, 1678.2 |
| 71 | δ9.50 (1H, t), 3.97 (2H, d), 3.62 (2H, s), 3.24-3.34 (2H, partially overlapped by water signal) 2.88-2.95 (1H, m), 2.78 (2H, t), 2.33 (3H, s), 1.05 (6H, d) | 395.0 (M$^+$ − 1) | IR (KBr, CM$^{-1}$): 3289.6, 1668.4, 1628.05 |

TABLE 1-continued

| Comp. No. | ¹H-NMR (400 MHz, DMSO-d₆) | MASS | IR (KBr, CM⁻¹) |
|---|---|---|---|
| 72 | δ 16.20 (1H, s), 9.69 (1H, t), 4.08 (2H, d), 3.34 (1H, merged with water signal), 3.10-3.20 (1H, m), 2.85-2.95 (1H, m), 2.75-2.81 (2H, m), 2.11-2.15 (1H, m), 1.78-1.82 (1H, m) | 366.1 (M⁺ − 1) | IR (KBr, CM⁻¹): 2976.8, 1733.1, 1684.8 |
| 73 | δ 9.50 (1H, t), 5.82 (1H, s), 4.54-4.56 (1H, m), 3.98 (2H, d), 3.35-3.60 (2H, partailly overlapped by water signal), 3.01-3.17 (2H, m), 2.35 (3H, s), 2.26 (3H, s), 2.09-2.20 (5H, m) | 446.0 (M⁺ − 1) | IR (KBr, CM⁻¹): 3261.1, 1743.2, 1663.7 |
| 74 | δ 16.01 (1H, s), 9.88 (1H, d), 4.49 (1H, dd), 3.17-3.19 (2H, m), 2.63-2.65 (2H, m), 1.90-2.00 (1H, m), 1.76-1.78(4H, m), 1.45-1.50 (1H, m), 1.20-1.25 (1H, m), 0.90-0.92 (6H, m) | 379.9 (M⁺ + 1) | IR (KBr, CM⁻¹): 3251.2, 1723.3, 1678.6 |
| 75 | δ 10.89 (1H, s), 9.65 (1H, t), 7.51 (1H, d), 7.32 (1H, d), 7.12 (1H, d), 7.05 (1H, t), 6.94 (1H, t), 4.70 (1H, q), 3.15-3.27 (4H, m), 2.63-2.67 (2H, m), 2.33 (3H, s), 1.75-1.79 (4H, m) | 482.8 (M⁺ + 1) | IR (KBr, CM⁻¹): 3279.2, 1669.8, 1621.7 |
| 76 | δ 9.63 (1H, d), 7.59 (1H, s), 6.84 (1H, s), 4.61(1H, q), 3.16-3.22 (2H, m), 2.89-3.08 (2H, m), 2.65-2.69 (2H, m), 2.32 (3H, s), 1.76-1.80 (4H, m) | 433.8 (M⁺ + 1) | IR (KBr, CM⁻¹): 3235.1, 1717.1, 1659.3 |
| 77 | δ 9.56 (1H, d), 9.24 (1H, s), 6.96 (2H, d), 6.64 (2H, d), 4.55-4.60 (1H, m), 3.17-3.21(2H, m), 2.87-3.02 (2H, m), 2.65-2.69 (2H, m), 2.32 (3H, s), 1.76-1.80 (4H, m) | 458.0 (M⁺ + 1) | IR (KBr, CM⁻¹): 3153.8, 1717.4, 1656.1 |
| 78 | δ 9.68(1H, t), 8.54 (2H, bs), 7.38 (2H, d), 4.08 (2H, d), 3.76 (2H, s), 3.57 (2H, s) 3.20-3.32 (2H, partially overlapped by water signal), 2.82 (2H, t) | 413.9 (M⁺ + 1) | IR (KBr, CM⁻¹): 3282.9, 1678.2, 1553.9 |
| 80 | δ 9.96 (1H, t), 3.42 (2H, d), 3.09 (2H, t), 2.26 (2H, s), 1.48 (2H, t), 0.98 (6H, s) | 350.2 (M⁺ − 1) | IR (KBr, CM⁻¹): 3284.1, 1658.2, 1612.6 |
| 82 | ¹H-NMR (400 MHz, D₂O): δ 3.80 (2H, s), 3.30-3.32 (2H, m), 2.54-2.57 (2H, m), 1.60-1.72 (6H, m) | 336.1 (M⁺ − 1) | IR (KBr, CM⁻¹): 3247.6, 1609.3, 1540.9 |
| 83 | δ 9.76 (2H, t), 8.99 (1H, bs), 7.85 (4H, bs), 3.88 (4H, d), 3.56-3.59 (5H, m), 3.31 (2H, t), 3.08-3.10 (2H, m), 2.75-2.77 (4H, m), 1.80-1.81 (4H, m), 1.62-1.64 (8H, m), 1.57-1.60 (2H, m) | 336.2 (M⁺ − 1) | IR (KBr, CM⁻¹): 3279.4, 1677.0, 1564.2 |
| 84 | ¹H-NMR (400 MHz, D₂O): δ 3.75 (2H, bs), 3.63 (1H, t), 3.27-3.29 (2H, m), 2.90 (2H, t), , 2.58-2.60 (2H, m), 1.57-1.81 (10H, m), 1.28-1.42 (2H, m) | 336.2 (M⁺ − 1) | IR (KBr, CM⁻¹): 2917.2, 1655.4, 1559.1 |
| 85 | ¹H-NMR (400 MHz, D₂O): δ 3.79 (2H, bs), 3.26-3.29 (2H, m), 2.50-2.52 (2H, m), 1.67-1.68 (2H, m), 1.57-1.60 (4H, m) | 336.1 (M⁺ − 1) | IR (KBr, CM⁻¹): 2921.7, 1656.6, 1562.5 |
| 86 | δ 9.79 (1H, bs), 3.88 (2H, d), 3.55-3.57 (2H, m), 2.66-2.68 (2H, m), 1.79-1.80 (2H, m), 1.69-1.71(4H, m), | 336.2 (M⁺ − 1) | IR (KBr, CM⁻¹): 2931.4, 1662.4, 1550.2 |
| 87 | δ 4.03-4.07 (2H, m), 3.55-3.66 (2H, m), 2.66-2.76 (2H, m), 1.78-1.87 (6H, m), | 336.2 (M⁺ − 1) | IR (KBr, CM⁻¹): 2933.6, 1678.9, 1558.7 |
| 88 | ¹H-NMR (400 MHz, D₂O): δ 3.78(2H, s), 3.28-3.30 (2H, m), 2.54-2.57 (2H, m), 1.60-1.70 (6H, m) | 338.0 (M⁺ + 1) | IR (KBr, CM⁻¹): 2743.3, 1663.9, 1590.0 |
| 89 | ¹H-NMR (400 MHz, D₂O): δ 3.80 (2H, s), 3.34-3.36 (2H, m), 2.96 (4H, q), 2.61-2.64 (2H, m), 1.67-1.77(6H, m), 1.15 (6H, t) | 336.2 (M⁺ − 1) | IR (KBr, CM⁻¹): 2933.4, 1673.3, 1650.6 |
| 90 | δ 9.78 (1H, s), 3.85-3.86 (2H, m), 3.66-3.68(2H, m), 3.50(2H, d), 3.42 (2H, t), 3.12 (9H, s), 2.70-2.72 (2H, m), 1.79-1.80 (2H, m), 1.69-1.70(4H, m), | 336.2 (M⁺ − 1) | IR (KBr, CM⁻¹): 2927.5, 1675.9, 1608.4 |
| 91 | δ 9.77 (1H, t), 3.70 (2H, d), 3.56-3.59 (2H, m), 3.46 (6H, merged with water peak), 2.74-2.76 (2H, m), 1.80-1.81 (2H, m), 1.69-1.71(4H, m), | 338.2 (M⁺ + 1) | IR (KBr, CM⁻¹): 2925.9, 1652.6, 1558.9 |
| 92 | ¹H-NMR (400 MHz, D₂O): δ 8.05 (1H, d), 7.08 (1H, d), 3.88 (1H, dd), 3.76 (2H, s), 3.28-3.30 (2H, m), 3.06-3.23 (2H, m), 2.60-2.61 (2H, m), 1.66-1.71(6H, m) | 338.0 (M⁺ + 1) | IR (KBr, CM⁻¹): 2949.4, 1740.7, 1679.2 |
| 93 | δ 9.45 (1H, t), 7.46 (1H, s), 7.12 (1H, s), 3.84 (2H, d), 3.59-3.61(2H, m), 2.79-2.81 (2H, m), 2.33 (3H, s), 1.81-1.82(2H, m), 1.70-1.71(4H, m) | 367.1 (M⁺ + 1) | IR (KBr, CM⁻¹): 3355.1, 1701.7, 1654.6 |
| 94 | δ 10.62 (1H, bs), 9.47 (1H, T), 8.89 (1H, s), 3.80 (2H, d), 3.59-3.61(2H, m), 2.79-2.81 (2H, m), 2.33(3H, s), 1.68-1.82 (6H, m), | 383.0 (M⁺ + 1) | IR (KBr, CM⁻¹): 3264.1, 1661.3, 1605.7 |
| 95 | ¹H-NMR (400 MHz, CDCl₃): δ 7.22-7.39 (4H, m), 5.45-5.49 (0.4H, m), 4.63-4.67(0.6H, m), 4.39-4.50(1H, m), 4.05-4.07(1H, m), 3.63-3.91 (3H, m), 2.75 (2H, bs), 2.55 (3H, d), 1.68-1.83 (6H, m), | 490.3 (M⁺ − 1) | IR (KBr, CM⁻¹): 2928.0, 1742.7, 1662.2 |
| 96 | ¹H-NMR (400 MHz, CDCl₃): δ 4.00-4.02 (1H, m), 3.74-3.78 (1H, m), 3.54-3.59 (2H, m), 3.40-3.44 (1H, m), 2.71 (2H, t), 2.50-2.56 (4H, m), 2.05-2.07 (2H, m), 1.24-1.91 (15H, m), | 462.3 (M⁺ − 1) | IR (KBr, CM-1): 2944.7, 1717.1, 1674.7 |
| 97 | ¹H-NMR (400 MHz, CDCl₃): δ 16.01 (1H, s), 10.23 (1H, t), 4.16 (2H, d), 3.65-3.67 (2H, m), 3.54 (2H, t), 3.44 (2H, t), 2.67-2.69 (2H, m), 2.00-2.03 (2H, m), 1.87-1.91 (4H, m), 1.74-1.76 (4H, m) | 391.1 (M⁺ + 1) | IR (KBr, CM⁻¹): 2931.1, 1677.2, 1566.0 |

TABLE 1-continued

| Comp. No. | $^1$H-NMR (400 MHz, DMSO-$d_6$) | MASS | IR (KBr, CM$^{-1}$) |
|---|---|---|---|
| 99 | $^1$H-NMR (400 MHz, CDCl$_3$): δ 15.63 (1H, s), 9.95 (1H, t), 7.26-7.35 (5H, m), 6.35 (1H, bs), 4.49 (2H, d), 4.14 (2H, d), 3.61-3.64 (2H, m), 2.69-2.72 (2H, m), 1.60-1.89 (6H, m), | 425.3 (M$^+$ − 1) | IR (KBr, CM$^{-1}$): 2932.3, 1685.6, 1533.9 |
| 100 | $^1$H-NMR (400 MHz, CDCl$_3$): δ 4.17-4.21 (2H, m), 3.62-3.64 (2H, m), 3.41-3.49 (3H, m), 2.69-2.71 (2H, m), 2.43 (2H, t), 1.41-2.04 (12H, m), 1.19-1.29 (2H, m) | 432.2 (M$^+$ − 1) | IR (KBr, CM$^{-1}$): 2926.3, 1730.5, 1678.2 |
| 101 | δ 12.02-12.52 (1H, m), 7.26-7.35 (5H, m), 4.71 (1H, s), 4.52 (1H, s), 3.66 (2H, d), 3.57-3.59 (2H, m), 2.67-2.73 (2H, m), 1.78-1.80 (2H, m), 1.66-1.68 (4H, m) | 426.2 (M$^+$ − 1) | IR (KBr, CM$^{-1}$): 2928.6, 1737.8, 1676.6 |

Combination Therapy

Compounds of the present invention may be administered in combination with other drugs that are used in the treatment/prevention/suppression or amelioration of the diseases or conditions for which compounds of Formula (I) are useful. Such other drugs may be administered contemporaneously or sequentially with a compound of Formula (I). When a compound of Formula (I) is used contemporaneously with one or more other drugs, a pharmaceutical composition containing such other drugs in addition to the compound of Formula (I) is preferred. Accordingly, the pharmaceutical compositions of the present invention include those that also contain one or more other active ingredients, in addition to a compound of Formula (I).

Pharmaceutical Compositions

In another embodiment of the invention, there is provided a pharmaceutical composition comprising a therapeutically effective amount of one or more of a compound of formula (I). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s) and at least one active ingredient. These dosage forms may be administered by a variety of routes including oral, topical, transdermal, subcutaneous, intramuscular, intravenous, intreperitoneal, intranasal, pulmonary etc.

Oral compositions may be in the form of solid or liquid dosage form. Solid dosage form may comprise pellets, pouches, sachets or discrete units such as tablets, multi-particulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients such as diluents, disintegrating agents, binders, solubilizers, lubricants, glidants, surfactants, suspending agents, emulsifiers, chelating agents, stabilizers, flavours, sweeteners, colours etc. Some example of suitable excipients include lactose, cellulose and its derivatives such as microcrystalline cellulose, methylcellulose, hydroxy propyl methyl cellulose & ethylcellylose, dicalcium phosphate, mannitol, starch, gelatin, polyvinyl pyrolidone, various gums like acacia, tragacanth, xanthan, alginates & its derivatives, sorbitol, dextrose, xylitol, magnesium Stearate, talc, colloidal silicon dioxide, mineral oil, glyceryl mono stearate, glyceryl behenate, sodium starch glycolate, cross povidone, crosslinked carboxymethylcellulose, various emulsifiers such as polyethylene glycol, sorbitol, fatty acid esters, polyethylene glycol alkylethers, sugar esters, polyoxyethylene polyoxypropyl block copolymers, polyethoxylated fatty acid monoesters, diesters and mixtures thereof.

Sterile compositions for injection can be formulated according to conventional pharmaceutical practice by dissolving or suspending the active substance in a vehicle such as water for injection, N-Methyl-2-Pyrrolidone, propylene glycol and other glycols, alcohols, a naturally occurring vegetable oil like sesame oil, coconut oil, peanut oil, cotton seed oil or a synthetic fatty vehicle like ethyl oleate or the like. Buffers, anti-oxidants, preservatives, complexing agents like cellulose derivatives, peptides, polypeptides and cyclodextrins and the like can be incorporated as required.

The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered orally or parenteraly at a dose of from 0.001 to 1500 mg/kg per day, preferably from 0.01 to 1500 mg/kg per day, more preferably from 0.1 to 1500 mg/kg per day, most preferably from 0.1 to 500 mg/kg per day. The dose range for adult humans is generally from 5 mg to 35 g per day and preferably 5 mg to 2 g per day.

Dosage forms of presentation provided in discrete units may conveniently contain an amount of compound of the invention which is effective at such dosage or as a multiple of the same, for example units containing 5 mg to 500 mg.

Examples of Pharmaceutical Composition

| No. | Ingredient | Quantity (%) |
|---|---|---|
| 1 | Compound no. 10 | 0.005 to 0.5 |
| 2 | Phosphate Buffer Saline pH 7.4 | Q.S. |

Accurately weighed quantity of compound no. 10 was dissolved in phosphate buffer saline (pH 7.4) under aseptic environment. The solution was filtered through 0.22 micron filter and filled into presterilized glass vials. The solution was purged with nitrogen during process. These vials were further terminally sterilized by autoclave.

Biological Testing:

In Vitro Erythropoietin Induction:

Hep3B cell line (ATCC HB8064) was employed. Induction of erythropoietin was carried out for the indicated dose of compounds for 16 hours duration. At the end of 16 hours, cell culture medium was collected and centrifuged to remove any debris. Supernatant obtained was analyzed for erythropoietin by ELISA (R&D systems, USA). The results were expressed as fold induction as compared to vehicle control.

TABLE 2

| Compound No. | Concentration uM | EPO fold induction |
|---|---|---|
| 1 | 50 | +++ |
| 2 | 200 | +++ |
| 3 | 200 | ++ |
| 4 | 200 | ++ |
| 5 | 200 | ++ |
| 6 | 200 | + |
| 7 | 200 | ++ |
| 8 | 200 | ++ |
| 9 | 200 | +++ |
| 10 | 200 | +++++ |
| 11 | 200 | +++ |
| 12 | 50 | ++ |
| 13 | 200 | + |
| 14 | 200 | ++ |
| 15 | 200 | + |
| 16 | 200 | +++ |
| 17 | 200 | ++ |
| 18 | 200 | ++++ |
| 19 | 200 | ++ |
| 20 | 200 | +++ |
| 21 | 200 | ++++ |
| 22 | 200 | +++ |
| 23 | 200 | ++++ |
| 24 | 200 | +++ |
| 25 | 200 | ++ |
| 26 | 200 | ++++ |
| 27 | 200 | ++++ |
| 28 | 200 | ++++ |
| 29 | 200 | ++++ |
| 30 | 200 | + |
| 31 | 200 | +++ |
| 32 | 200 | ++++ |
| 33 | 200 | ++ |
| 34 | 200 | +++++ |
| 35 | 200 | + |
| 36 | 12.5 | + |
| 37 | 200 | +++ |
| 38 | 200 | ++++ |
| 39 | 200 | ++ |
| 40 | 200 | +++ |
| 41 | 200 | ++ |
| 42 | 200 | +++ |
| 43 | 200 | + |
| 44 | 200 | + |
| 46 | 50 | ++ |
| 49 | 200 | +++ |
| 53 | 200 | + |
| 54 | 200 | + |
| 55 | 200 | + |
| 52 | 200 | +++ |
| 56 | 200 | + |
| 57 | 200 | + |
| 58 | 200 | +++ |
| 59 | 200 | + |
| 60 | 200 | +++ |
| 61 | 200 | + |
| 64 | 200 | + |
| 65 | 200 | +++ |
| 67 | 200 | ++ |
| 70 | 200 | ++ |
| 72 | 200 | + |
| 80 | 200 | ++++ |
| 82 | 50 | ++++ |

+ indicates <2 fold;
++ indicates 2-4 fold;
+++ indicates 5-8 fold;
++++ indicates 9-16 fold;
+++++ indicates >16 fold induction of erythropoietin respectively, relative to vehicle control.

Above data indicates that the compounds of the present invention significantly elevate the expression of erythropoietin in cells.

In Vitro Induction of Adrenomedullin:

Hep3B cell line (ATCC HB8064) was employed. Induction of adrenomedullin was carried out for the indicated dose of compounds for 6 hours duration. At the end of 6 hours, cells were lysed and total RNA was isolated. Expression of adrenomedullin mRNA along-with expression of 18S rRNA was monitored by real-time PCR. Adrenomedullin mRNA expression was normalized relative to the expression of 18S rRNA. The results were expressed as fold induction of adrenomedullin mRNA relative to vehicle treated control.

TABLE 3

| Compound No. | Concentration (uM) | Adrenomedullin mRNA (fold induction) |
|---|---|---|
| 10 | 200 | ++++ |
| 23 | 200 | ++ |
| 27 | 200 | ++++ |
| 32 | 200 | ++ |
| 34 | 200 | +++ |
| 49 | 200 | +++ |
| 52 | 200 | +++ |
| 82 | 200 | +++ |

+ indicates <2 fold;
++ indicates 2-4 fold;
+++ indicates 5-8 fold;
++++ indicates >8 fold induction of adrenomedullin mRNA respectively, relative to vehicle control.

Above data indicates that the compounds of the present invention significantly elevate the expression of adrenomedullin in cells.

In Vitro Induction of Vascular Endothelial Growth Factor (VEGF):

Hep3B cell line (ATCC HB8064) was employed. Induction of VEGF was carried out for the indicated dose of compounds for 16 hours duration. At the end of 16 hours, cell culture medium was collected and centrifuged to remove any debris. Supernatant obtained was analyzed for VEGF by ELISA (R&D systems, USA). The results were expressed as fold induction as compared to vehicle control.

TABLE 4

| Compound No. | Concentration (uM) | VEGF (Fold induction) |
|---|---|---|
| 10 | 200 | ++ |
| 23 | 200 | ++ |
| 27 | 200 | ++ |
| 32 | 200 | ++ |
| 34 | 200 | ++ |
| 82 | 200 | ++ |

+ indicates <2 fold;
++ indicates 2-4 fold induction of VEGF relative to vehicle control Above data indicates that the compounds of the present invention significantly elevate the expression of VEGF in cells.

Effect of Compounds of Present Invention on Anemia Associated with Chronic Kidney Disease (CKD):

The efficacy of the test compound to correct anemia associated with CKD was studied in an animal model of anemia—5/6 nephrectomized (5/6 NX) rats[15,16,17]. Animals were randomized based upon anemia and kidney dysfunction parameters and divided into two groups. One group received compound 10 (20 mg/kg; b.i.d. i.p) for seven days while the control received respective vehicle. Blood sampling was done on day 3 and 7 post initiation of drug administration to check early markers of anemia correction.

Results:

Treatment with the test compound resulted in significant increase in circulating EPO levels ranging from 115-3900 pg/ml as compared with undetectable levels (<45 pg/ml) of circulating EPO in vehicle control. There was 3 and 5.6 fold increase in reticulocyte production index on day 3 and day 7 respectively compared to control group with test compound treatment. Similarly, there was 30%, 25% and 24% increase in hemoglobin content, hematocrit percent and erythrocyte count respectively on day 7 of treatment compared to control.

Effect of Compound of Present Invention on Ischemia-Reperfusion Injury to Kidney:

The efficacy of test compound to improve renal function was evaluated in a renal ischemia and reperfusion induced acute kidney injury model in rats. The beneficial effect of the compound was evaluated using two different treatment protocols. In one protocol treatment with test compound was given before onset of ischemia (pre-treatment) and the other protocol involved treatment with test compound initiated after the onset of ischemia (post-treatment).

Pre-ischemia intervention protocol: Rats were randomised into two groups, compound treated and vehicle control. Before initiation of bilateral renal ischemia, the animals in compound treatment group received multiple doses of compound no. 10 (i.e. pre treated) and control group received vehicle by i.p route.

Post-ischemia intervention protocol: Rats were randomised into two groups, compound treated and vehicle control. After initiation of bilateral renal ischemia, the animals in compound treatment group received multiple doses of compound no. 10 (i.e. post treated) and control group received vehicle in similar fashion by i.p route.

Induction of Renal Ischemia and Reperfusion in Rats:

All animals were anesthetized with pentobarbital sodium (50 mg/kg body wt). Homeothermic blanket was used to maintain a constant body temperature of 37° C. during surgery and ischemia. A midline incision was made at the ventral side to access the kidneys and both renal pedicle were isolated and occluded for 35 mins using microclips, which was verified by the change of the renal color. After an ischemic period of 35 min, the microclips were removed and reperfusion initiated. The abdomen was closed and skin & muscles sutured and animal allowed to recover. Blood sample of 300 µl was taken via sublingual vein puncture at various predetermined time points.

Results:

In both protocols tested i.e pre-ischemia intervention and post-ischemia intervention, renal function improvement was assessed by measuring serum creatinine and BUN (blood urea nitrogen) at various time points post ischemia. Results are expressed below as % reduction from their control group at 24 hrs post initiation of ischemia.

TABLE 5

| Compound No. | i.p. Dose (mg/kg) | % reduction | |
|---|---|---|---|
| | | Ser. Creatinine | BUN |
| Compound-10 (Multiple dose) | 10 | 33.0 | 18.0 |

Pre-Ischemia Intervention:

TABLE 6

| Compound No. | i.p.Dose (mg/kg) | % reduction | |
|---|---|---|---|
| | | Ser. Creatinine | BUN |
| Compound-10 (Multiple dose) | 0.3 mg/kg as 1st dose & 0.1 mg/kg as subsequent dose | 31.0 | 17.0 |

REFERENCES

1. Schofield C J & Ratcliffe P J (2004) Nature Review Molecular Cell Biology; 5; 343-354
2. Scmenza G L (2000) J Appl Physiol; 88; 1474-1480
3. Weidemann A et al. (2008) J Am Soc Nephrol; 19; 486-494
4. Bernhardt W M et al. (2006) J Am Soc Nephrol; 17; 1970-1978
5. Hill P et al (2008) J Am Soc Nephrol; 19; 39-46
6. Siddiq A et al. (2005) J Biol Chem; 280; 50; 41732-43
7. Nangaku M (2007) J Am Soc Nephrol; 18; 13-15
8. Amador A et al. (2007) Am J Transplantation; 7; 2180-2189
9. Fisher J W (2003) Exp Biol Med; 228; 1-14
10. Binley K et al. (2002) Blood; 100; 2406-2413
11. Luo Y H et al. (2009) Hepatobiliary Pancreat Dis Int; 8; 294-299
12. Siren A L et al. (2000) PNAS; 98; 7; 4044-49
13. Sharples E J et al. (2004) J Am Soc Nephrol; 15; 2115-2124
14. Looi Y H et al. (2006) Br J Pharmacol; 148; 599-609
15. Hahn S, et al (1999); Pediatr Nephrol; 13; 195-198
16. Priyadarshi A, et al (2002) Kidney Int; 61; 542-546
17. Shapiro J I, et al (1990) Am J Physiol; 258; 183-188

We claim:

1. A method of treating anemia in a subject in need thereof, comprising:
   administering a therapeutically effective amount of a compound of formula (I)

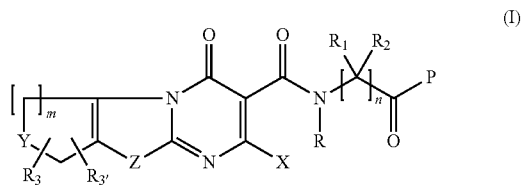

(I)

their pharmaceutically acceptable salts and their isomers, stereoisomers, conformers, tautomers, and polymorphs;
Wherein,
When Y is $NR_4$, O, S or $SO_2$, m is 1 to 2 and when Y is $C(R_5)(R_6)$, m is 1 to 4;
n is 1 to 6;
P is —OH, —$OR_7$, —$NH_2$, —$NHR_7$, —$NR_7R_7'$, —$NHSO_2R_7$, —$NHCOR_7$, —NHOH or —$NHOR_7$;
X is —OH, —$OR_7$, —$SR_7$, —$SOR_7$, —$SO_2R_7$, —$NHR_7$ or —$NR_7R_7'$;
Z is S or O;
R is hydrogen, linear or branched $(C_1$-$C_8)$alkyl, —$(C_1$-$C_8)$alkylaryl or —$(C_1$-$C_8)$alkylheteroaryl;
$R_1$ and $R_2$ are independently selected from hydrogen, linear or branched —$(C_1$-$C_8)$alkyl, —$(C_3$-$C_7)$ cycloalkyl, aryl, heteroaryl, —$CH_2$-aryl and —$CH_2$-heteroaryl, or $R_1$ and $R_2$ may join together to form a 3-6 membered monocyclic or 9-12 membered bicyclic ring;

R together with either $R_1$ or $R_2$ of adjacent carbon atom may form a 3-6 membered monocyclic or 8-11 membered bicyclic heteroaryl or heterocyclyl ring;

$R_3$ and $R_{3'}$ at each occurrence is independently selected from hydrogen, linear or branched $(C_1-C_8)$alkyl, $(C_1-C_5)$ alkoxy and halo;

$R_3$ and $R_{3'}$ may also present in gem di-halo, gem di-alkyl or spirocycloalkyl arrangement;

$R_4$ is selected from the group consisting of hydrogen, linear or branched $(C_1-C_8)$ alkyl, $(C_3-C_7)$ cycloalkyl, aryl, heteroaryl, —$(C_1-C_8)$ alkyl-aryl, —$(C_1-C_8)$alkyl-heteroaryl, —$(C_1-C_2)$alkyl-heterocyclyl, —C(O)$R_8$, —C(O)O$R_8$, —C(O)N$R_8R_9$, —C(S)N$R_8R_9$ and —SO$_2R_8$, wherein aryl and heteroaryl radicals are optionally substituted with one or more substituent selected from the group consisting of —$(C_1-C_8)$ alkyl, —$(C_3-C_7)$ cycloalkyl, heterocyclyl, aryl, heteroaryl, —OH, —alkoxy, halo, CN, —CF$_3$, —OCF$_3$, —O-aryl, —SO$_2$—$(C_1-C_8)$-alkyl, —SO$_2$-aryl, —NH$_2$, —NHR$_{10}$, —NR$_{10}$R$_{10'}$, —NH—CO—$(C_1-C_8)$ alkyl, —NH—SO$_2$—$(C_1-C_8)$alkyl, —NH—SO$_2$-aryl, —COOH, —C(O)NH-alkyl, —CONH-aryl, —CONH-heteroaryl, —C(O)O—$(C_1-C_8)$alkyl, —C(O)O-aryl, —SO$_2$NH—$(C_1-C_8)$alkyl, —SO$_2$NH-aryl and —SO$_2$NH-heteroaryl;

$R_5$ and $R_6$ are independently selected from the group consisting of hydrogen, linear or branched $(C_1-C_8)$alkyl, $(C_3-C_7)$ cycloalkyl, aryl, heteroaryl, fluoro, —COOH, —CONH—$(C_1-C_8)$alkyl, —NHCO—$(C_1-C_8)$alkyl, —NHCO-aryl, —NHCO-heteroaryl, —NH—SO$_2$($C_1$-$C_8$)alkyl, —NH—SO$_2$-aryl and —NH—SO$_2$-heteroaryl;

$R_5$ and $R_6$ may join together to form a 3-6 membered carbocyclic, heteroaryl or heterocyclyl ring;

$R_7$, $R_{7'}$, $R_{10}$ and $R_{10'}$ are independently selected from linear or branched $(C_1-C_8)$alkyl, $(C_3-C_7)$ cycloalkyl and —$(C_1-C_8)$alkylaryl;

$R_7$ and $R_{7'}$ or $R_{10}$ and $R_{10'}$ together with nitrogen atom to which they are attached, may form 5-6 membered monocyclic or 8-14 membered bicyclic saturated and partially saturated ring, the ring may contain 1 to 3 heteroatom selected from N, S & O; wherein saturated and partially saturated ring may be optionally substituted with one or more substituent independently selected from the group consisting of —$(C_1-C_8)$alkyl, —$(C_3-C_7)$ cycloalkyl, heterocyclyl, aryl, heteroaryl, —OH, -alkoxy, halo, —CN, —CF$_3$, —OCF$_3$, —O-aryl, —SO$_2$—$(C_1-C_8)$-alkyl, —SO$_2$-aryl, —NH$_2$, —NHR$_{10}$, —NR$_{10}$R$_{10'}$, —NH—CO—$(C_1-C_8)$alkyl, —NH—SO$_2$—$(C_1-C_8)$ alkyl, —NH—SO$_2$-aryl, —COOH, —C(O)NH-alkyl, —CONH-aryl, —CONH-heteroaryl, —C(O)O—$(C_1-C_8)$alkyl, —C(O)O-aryl, —SO$_2$NH—$(C_1-C_8)$alkyl, —SO$_2$NH-aryl and —SO$_2$NH-heteroaryl;

$R_8$ is selected from the group consisting of linear or branched $(C_1-C_8)$ alkyl, $(C_3-C_7)$ cycloalkyl, —$(C_1-C_8)$ alkyl-$(C_3-C_7)$cycloalkyl, heterocyclyl, aryl, -$(C_1-C_8)$ alkyl-aryl, —$(C_1-C_2)$alkyl-heterocyclyl, heteroaryl and —$(C_1-C_8)$alkyl-heteroaryl, wherein aryl and heteroaryl radicals are optionally substituted with one or more substituent selected from linear or branched $(C_1-C_8)$alkyl, $(C_3-C_7)$cycloalkyl, —$(C_1-C_8)$alkyl-$(C_3-C_7)$cycloalkyl, aryl, heteroaryl, heterocyclyl, —OH, alkoxy, halo, —CN, —CF$_3$, —OCF$_3$, —O-aryl, —SO$_2$—$(C_1-C_8)$ alkyl, —SO$_2$-aryl, —NH$_2$, —NHR$_{10}$, —NR$_{10}$R$_{10'}$, —NH—CO—$(C_1-C_8)$alkyl, —NH—SO$_2$—$(C_1-C_8)$ alkyl, —C(O)OH, —C(O)NH—$(C_1-C_8)$alkyl, —CONH-aryl, —CONH-heteroaryl, —NHCONH—$(C_1-C_8)$alkyl, —NHCONH-aryl, —SO$_2$NH—$(C_1-C_8)$ alkyl, —SO$_2$NH-aryl and —SO$_2$NH-heteroaryl;

$R_9$ is hydrogen, linear or branched $(C_1-C_8)$alkyl or —$(C_1-C_8)$alkylaryl;

$R_8$ and $R_9$ together with nitrogen atom to which they are attached, may form 5-6 membered saturated ring.

2. The method of claim 1, wherein the anemia comprises anemia of elderly or anemia associated with conditions like chronic diseases, renal failure, cancer, infection, dialysis, surgery, and chemotherapy.

3. The method of claim 1, wherein the compound of formula (I) is selected from the group consisting of:

[(2-Hydroxy-4-oxo-5,6,7,8-tetrahydro-4H-9-thia-1,4a-diaza-fluorene-3-carbonyl)-amino]-acetic acid;

3-(Carboxymethyl-carbamoyl)-2-hydroxy-4-oxo-5,8-dihydro-4H,6H-9-thia-1,4a,7-triaza-fluorene-7-carboxylic acid ethyl ester;

[(2-Hydroxy-7-methanesulfonyl-4-oxo-5,6,7,8-tetrahydro-4H-9-thia-1,4a,7-triaza-fluorene-3-carbonyl)-amino]-acetic acid;

{[2-Hydroxy-7-(3-methyl-butyryl)-4-oxo-5,6,7,8-tetrahydro-4H-9-thia-1,4a,7-triaza-fluorene-3-carbonyl]-amino}-acetic acid;

{[2-Hydroxy-4-oxo-7-(propane-2-sulfonyl)-5,6,7,8-tetrahydro-4H-9-thia-1,4a,7-triaza-fluorene-3-carbonyl]-amino}-acetic acid;

1-[(2-Hydroxy-4-oxo-5,6,7,8-tetrahydro-4H-9-thia-1,4a-diaza-fluorene-3-carbonyl)-amino]-cyclopentanecarboxylic acid;

{[2-Hydroxy-4-oxo-7-(toluene-4-sulfonyl)-5,6,7,8-tetrahydro-4H-9-thia-1,4a,7-triaza-fluorene-3-carbonyl]-amino}-acetic acid;

[(2-Hydroxy-4-oxo-7-phenylcarbamoyl-5,6,7,8-tetrahydro-4H-9-thia-1,4a,7-triaza-fluorene-3-carbonyl)-amino]-acetic acid;

[(7-Cyclopropanecarbonyl-2-hydroxy-4-oxo-5,6,7,8-tetrahydro-4H-9-thia-1,4a,7-triaza-fluorene-3-carbonyl)-amino]-acetic acid;

[(2-Hydroxy-4-oxo-6,7,8,9-tetrahydro-4H,5H-10-thia-1,4a-diaza-benzo[a]azulene-3-carbonyl)-amino]-acetic acid;

[(2-Hydroxy-4-oxo-7,8-dihydro-4H,6H-cyclopenta[4,5]thiazolo[3,2-a]pyrimidine-3-carbonyl)-amino]-acetic acid;

[(2-Hydroxy-4-oxo-5,6,7,8-tetrahydro-4H-9-thia-1,4a-diaza-fluorene-3-carbonyl)-amino]-acetic acid, sodium salt;

[(7-tert-Butyl-2-hydroxy-4-oxo-5,6,7,8-tetrahydro-4H-9-thia-1,4a-diaza-fluorene-3-carbonyl)-amino]-acetic acid;

3-[(2-Hydroxy-4-oxo-7,8-dihydro-4H,6H-cyclopenta[4,5]thiazolo[3,2-a]pyrimidine-3-carbonyl)-amino]-propionic acid;

3-[(7-tert-Butyl-2-hydroxy-4-oxo-5,6,7,8-tetrahydro-4H-9-thia-1,4a-diaza-fluorene-3-carbonyl)-amino]-propionic acid;

{[7-(4-Fluoro-benzoyl)-2-hydroxy-4-oxo-5,6,7,8-tetrahydro-4H-9-thia-1,4a,7-triaza-fluorene-3-carbonyl]-amino}-acetic acid;

{[7-(5-Chloro-thiophene-2-sulfonyl)-2-hydroxy-4-oxo-5,6,7,8-tetrahydro-4H-9-thia-1,4a,7-triaza-fluorene-3-carbonyl]-amino}-acetic acid;

{[2-Hydroxy-4-oxo-7-(5-trifluoromethyl-pyridin-2-yl)-5,6,7,8-tetrahydro-4H-9-thia-1,4a,7-triaza-fluorene-3-carbonyl]-amino}-acetic acid;

{[2-Hydroxy-4-oxo-7-(4-trifluoromethoxy-benzenesulfonyl)-5,6,7,8-tetrahydro-4H-9-thia-1,4a,7-triaza-fluorene-3-carbonyl]-amino}-acetic acid;

{[7-(2,2-Dimethyl-propionyl)-2-hydroxy-4-oxo-5,6,7,8-tetrahydro-4H-9-thia-1,4a,7-triaza-fluorene-3-carbonyl]-amino}-acetic acid;

{[7-(4-Butyl-benzoyl)-2-hydroxy-4-oxo-5,6,7,8-tetrahydro-4H-9-thia-1,4a,7-triaza-fluorene-3-carbonyl]-amino}-acetic acid;

{[2-Hydroxy-4-oxo-7-(4-trifluoromethoxy-benzoyl)-5,6,7,8-tetrahydro-4H-9-thia-1,4a,7-triaza-fluorene-3-carbonyl]-amino}-acetic acid;

{[7-(4-Chloro-benzyl)-2-hydroxy-4-oxo-5,6,7,8-tetrahydro-4H-9-thia-1,4a,7-triaza-fluorene-3-carbonyl]-amino}-acetic acid;

{[7-(4-Fluoro-phenylthiocarbamoyl)-2-hydroxy-4-oxo-5,6,7,8-tetrahydro-4H-9-thia-1,4a,7-triaza-fluorene-3-carbonyl]-amino}-acetic acid;

[(2-Hydroxy-7-isopropylthiocarbamoyl-4-oxo-5,6,7,8-tetrahydro-4H-9-thia-1,4a,7-triaza-fluorene-3-carbonyl)-amino]-acetic acid;

3-(Carboxymethyl-carbamoyl)-2-hydroxy-4-oxo-5,8-dihydro-4H,6H-9-thia-1,4a,7-triaza-fluorene-7-carboxylic acid benzyl ester;

{[7-(2-Cyclopropyl-acetyl)-2-hydroxy-4-oxo-5,6,7,8-tetrahydro-4H-9-thia-1,4a,7-triaza-fluorene-3-carbonyl]-amino}-acetic acid;

({7-[2-(4-Chloro-phenyl)-acetyl]-2-hydroxy-4-oxo-5,6,7,8-tetrahydro-4H-9-thia-1,4a,7-triaza-fluorene-3-carbonyl}-amino)-acetic acid;

{[7-(2-Cyclopentyl-acetyl)-2-hydroxy-4-oxo-5,6,7,8-tetrahydro-4H-9-thia-1,4a,7-triaza-fluorene-3-carbonyl]-amino}-acetic acid;

3-[(2-Hydroxy-4-oxo-6,7,8,9-tetrahydro-4H,5H-10-thia-1,4a-diaza-benzo[a]azulene-3-carbonyl)-amino]-propionic acid;

{[2-Hydroxy-7-(4-methoxy-benzyl)-4-oxo-5,6,7,8-tetrahydro-4H-9-thia-1,4a,7-triaza-fluorene-3-carbonyl]-amino}-acetic acid;

2-[(2-Hydroxy-4-oxo-6,7,8,9-tetrahydro-4H,5H-10-thia-1,4a-diaza-benzo[a]azulene-3-carbonyl)-amino]-propionic acid;

{[7-(6-Chloro-pyridine-3-carbonyl)-2-hydroxy-4-oxo-5,6,7,8-tetrahydro-4H-9-thia-1,4a,7-triaza-fluorene-3-carbonyl]-amino}-acetic acid;

[(2-Hydroxy-7,7-dimethyl-4-oxo-5,6,7,8-tetrahydro-4H-9-thia-1,4a-diaza-fluorene-3-carbonyl)-amino]-acetic acid;

{[7-(6-Chloro-pyridazin-3-yl)-2-hydroxy-4-oxo-5,6,7,8-tetrahydro-4H-9-thia-1,4a,7-triaza-fluorene-3-carbonyl]-amino}-acetic acid;

{[7-(3-Cyano-pyridin-2-yl)-2-hydroxy-4-oxo-5,6,7,8-tetrahydro-4H-9-thia-1,4a,7-triaza-fluorene-3-carbonyl]-amino}-acetic acid;

{[7-(3-Chloro-4-methoxy-benzoyl)-2-hydroxy-4-oxo-5,6,7,8-tetrahydro-4H-9-thia-1,4a,7-triaza-fluorene-3-carbonyl]-amino}-acetic acid;

[(2-Hydroxy-4-oxo-5,6,7,8,9,10-hexahydro-4H-11-thia-1,4a-diaza-cycloocta[a]indene-3-carbonyl)-amino]-acetic acid;

[(2-Hydroxy-7-indan-5-ylmethyl-4-oxo-5,6,7,8-tetrahydro-4H-9-thia-1,4a,7-triaza-fluorene-3-carbonyl)-amino]-acetic acid;

2-[(2-Hydroxy-7,7-dimethyl-4-oxo-5,6,7,8-tetrahydro-4H-9-thia-1,4a-diaza-fluorene-3-carbonyl)-amino]-propionic acid;

{[7-(3,5-Dimethoxy-benzoyl)-2-hydroxy-4-oxo-5,6,7,8-tetrahydro-4H-9-thia-1,4a,7-triaza-fluorene-3-carbonyl]-amino}-acetic acid;

{[2-Hydroxy-7-(4-methanesulfonyl-benzoyl)-4-oxo-5,6,7,8-tetrahydro-4H-9-thia-1,4a,7-triaza-fluorene-3-carbonyl]-amino}-acetic acid;

2-[(2-Hydroxy-7,7-dimethyl-4-oxo-5,6,7,8-tetrahydro-4H-9-thia-1,4a-diaza-fluorene-3-carbonyl)-amino]-3-methyl-butyric acid (L-isomer);

2-[(2-Hydroxy-7,7-dimethyl-4-oxo-5,6,7,8-tetrahydro-4H-9-thia-1,4a-diaza-fluorene-3-carbonyl)-amino]-propionic acid (D-isomer);

{[7-(3,5-Bis-trifluoromethyl-benzyl)-2-hydroxy-4-oxo-5,6,7,8-tetrahydro-4H-9-thia-1,4a,7-triaza-fluorene-3-carbonyl]-amino}-acetic acid;

{[7-(3,4-Dichloro-benzyl)-2-hydroxy-4-oxo-5,6,7,8-tetrahydro-4H-9-thia-1,4a,7-triaza-fluorene-3-carbonyl]-amino}-acetic acid;

{[2-Hydroxy-4-oxo-7-(4-trifluoromethyl-benzyl)-5,6,7,8-tetrahydro-4H-9-thia-1,4a,7-triaza-fluorene-3-carbonyl]-amino}-acetic acid;

[(7,7-Diethyl-2-hydroxy-4-oxo-5,6,7,8-tetrahydro-4H-9-thia-1,4a-diaza-fluorene-3-carbonyl)-amino]-acetic acid;

2-[(2-Hydroxy-7,7-dimethyl-4-oxo-5,6,7,8-tetrahydro-4H-9-thia-1,4a-diaza-fluorene-3-carbonyl)-amino]-2-methyl-propionic acid;

[(2-Hydroxy-7,7-dimethyl-4-oxo-5,6,7,8-tetrahydro-4H-9-thia-1,4a-diaza-fluorene-3-carbonyl)-amino]-phenyl-acetic acid, L-isomer;

[(7-Benzoylamino-2-hydroxy-4-oxo-5,6,7,8-tetrahydro-4H-9-thia-1,4a-diaza-fluorene-3-carbonyl)-amino]-acetic acid;

[(2-Hydroxy-4-oxo-5,6,7,8-tetrahydro-4H-9-oxa-1,4a-diaza-fluorene-3-carbonyl)-amino]-acetic acid;

[(2-Hydroxy-7-methyl-4-oxo-5,6,7,8-tetrahydro-4H-9-thia-1,4a-diaza-fluorene-3-carbonyl)-amino]-acetic acid;

[(2-Hydroxy-4-oxo-7-propyl-5,6,7,8-tetrahydro-4H-9-thia-1,4a-diaza-fluorene-3-carbonyl)-amino]-acetic acid;

[(2-Hydroxy-6,6-dimethyl-4-oxo-5,6,7,8-tetrahydro-4H-9-thia-1,4a-diaza-fluorene-3-carbonyl)-amino]-acetic acid;

[(2-Hydroxy-7,7-dimethyl-4-oxo-5,6,7,8-tetrahydro-4H-9-thia-1,4a-diaza-fluorene-3-carbonyl)-methyl-amino]-acetic acid;

[(2-Hydroxy-4-oxo-7-phenyl-5,6,7,8-tetrahydro-4H-9-thia-1,4a-diaza-fluorene-3-carbonyl)-amino]-acetic acid;

[(2-Hydroxy-4-oxo-5,8-dihydro-4H,6H-7-oxa-9-thia-1,4a-diaza-fluorene-3-carbonyl)-amino]-acetic acid;

[(2-Hydroxy-4,7,7-trioxo-5,6,7,8-tetrahydro-4H-7lambda*6*,9-dithia-1,4a-diaza-fluorene-3-carbonyl)-amino]-acetic acid;

N-[(2'-hydroxy-4'-oxo-6',9'-dihydro-4'H,7'H-spiro[cyclopropane-1,8'-pyrimido[2,1-b][1,3]benzothiazol]-3'-yl)carbonyl]glycine;

3-(Carboxymethyl-carbamoyl)-2-hydroxy-4-oxo-5,6,7,8-tetrahydro-4H-9-thia-1,4a-diaza-fluorene-7-carboxylic acid;

[(2-Hydroxy-7,7-dimethyl-4-oxo-5,6,7,8-tetrahydro-4H-9-thia-1,4a-diaza-fluorene-3-carbonyl)-amino]-acetic acid, Disodium salt;

[(2-Hydroxy-4-oxo-6,7,8,9-tetrahydro-4H,5H-10-thia-1,4a-diaza-benzo[a]azulene-3-carbonyl)-amino]-acetic acid, Disodium salt; and pharmaceutically acceptable salts thereof.

4. A method of treatment of ischemic disorder selected from acute kidney injury, myocardial infarction, stroke, hepatic ischemia-reperfusion injury and peripheral vascular disease in a subject in need thereof, the method comprising: administering to the subject a therapeutically effective amount of [(2-Hydroxy-4-oxo-6,7,8,9-tetrahydro-4H,5H-10-thia-1,4a-diaza-benzo[a]azulene-3-carbonyl)-amino]-acetic acid.

5. A method of treatment of according to claim 4 wherein ischemic disorder is acute kidney injury.

6. A method of treating anemia in a subject in need thereof, comprising: administering to the subject a therapeutically effective amount of [(2-Hydroxy-4-oxo-6,7,8,9-tetrahydro-4H,5H-10-thia-1,4a-diaza-benzo[a]azulene-3-carbonyl)-amino]-acetic acid.

\* \* \* \* \*